(12) United States Patent
Sällberg et al.

(10) Patent No.: US 7,261,883 B2
(45) Date of Patent: *Aug. 28, 2007

(54) VACCINES CONTAINING RIBAVIRIN AND METHODS OF USE THEREOF

(75) Inventors: Matti Sällberg, Alvsjo (SE); Catharina Hultgren, Stockholm (SE)

(73) Assignee: Tripep AB, Huddinge (SE)

( * ) Notice: Subject to any disclaimer, the term of this patent is extended or adjusted under 35 U.S.C. 154(b) by 212 days.

This patent is subject to a terminal disclaimer.

(21) Appl. No.: 10/719,619

(22) Filed: Nov. 20, 2003

(65) Prior Publication Data

US 2004/0086529 A1    May 6, 2004

Related U.S. Application Data

(63) Continuation of application No. 10/104,966, filed on Mar. 22, 2002, now Pat. No. 6,680,059, which is a continuation of application No. 09/705,547, filed on Nov. 3, 2000, now abandoned.

(60) Provisional application No. 60/229,175, filed on Aug. 29, 2000.

(51) Int. Cl.
*A61K 39/29*    (2006.01)
*A61K 48/00*    (2006.01)

(52) U.S. Cl. .................... 424/93.1; 424/228.1

(58) Field of Classification Search ........... 424/93.1, 424/189.1, 225.1, 226.1, 227.1, 228.1
See application file for complete search history.

(56) References Cited

U.S. PATENT DOCUMENTS

| | | | |
|---|---|---|---|
| 4,215,051 A | 7/1980 | Schroeder et al. |
| 4,376,110 A | 3/1983 | David et al. |
| 4,486,530 A | 12/1984 | David et al. |
| 4,683,195 A | 7/1987 | Mullis et al. |
| 4,683,202 A | 7/1987 | Mullis |
| 4,818,540 A | 4/1989 | Chien et al. |
| 4,873,191 A | 10/1989 | Wagner et al. |
| 4,946,778 A | 8/1990 | Ladner et al. |
| 4,950,647 A | 8/1990 | Robins et al. |
| 4,965,188 A | 10/1990 | Mullis |
| 5,143,854 A | 9/1992 | Pirrung et al. |
| 5,290,678 A | 3/1994 | Jackowski |
| 5,322,770 A | 6/1994 | Gelfand |
| 5,350,671 A | 9/1994 | Houghton et al. |
| 5,371,017 A | 12/1994 | Houghton et al. |
| 5,372,928 A | 12/1994 | Miyamura et al. |
| 5,412,087 A | 5/1995 | McGall et al. |
| 5,585,258 A | 12/1996 | Houghton et al. |
| 5,589,466 A | 12/1996 | Felgner et al. |
| 5,593,972 A | 1/1997 | Weiner et al. |
| 5,597,691 A | 1/1997 | Houghton et al. |
| 5,604,105 A | 2/1997 | Jackowski |
| 5,670,152 A | 9/1997 | Weiner et al. |
| 5,670,153 A | 9/1997 | Weiner et al. |
| 5,679,342 A | 10/1997 | Houghton et al. |
| 5,683,864 A | 11/1997 | Houghton et al. |
| 5,698,390 A | 12/1997 | Houghton et al. |
| 5,710,008 A | 1/1998 | Jackowski |
| 5,712,087 A | 1/1998 | Houghton et al. |
| 5,712,088 A | 1/1998 | Houghton et al. |
| 5,712,145 A | 1/1998 | Houghton et al. |
| 5,714,596 A | 2/1998 | Houghton et al. |
| 5,728,520 A | 3/1998 | Weiner et al. |
| 5,739,118 A | 4/1998 | Carrano et al. |
| 5,744,358 A | 4/1998 | Jackowski |
| 5,747,274 A | 5/1998 | Jackowski |
| 5,756,312 A | 5/1998 | Weiner et al. |
| 5,766,845 A | 6/1998 | Weiner et al. |
| 5,767,097 A | 6/1998 | Tam |
| 5,847,101 A | 12/1998 | Okayama et al. |
| 5,856,437 A | 1/1999 | Miyamura et al. |
| 5,863,719 A | 1/1999 | Houghton et al. |
| 5,871,903 A | 2/1999 | Miyamura et al. |
| 5,879,904 A | 3/1999 | Brechot et al. |
| 5,885,799 A | 3/1999 | Houghton et al. |
| 5,932,556 A | 8/1999 | Tam |
| 5,942,234 A | 8/1999 | Ralston et al. |
| 5,959,092 A | 9/1999 | Miyamura et al. |
| 5,968,775 A | 10/1999 | Houghton et al. |
| 5,989,905 A | 11/1999 | Houghton et al. |
| 6,027,729 A | 2/2000 | Houghton et al. |
| 6,056,961 A | 5/2000 | Lavie et al. |

(Continued)

FOREIGN PATENT DOCUMENTS

EP    0 388 232    9/1990

(Continued)

OTHER PUBLICATIONS

Steigerwald-Mullen et al. J. Virol. 2000, vol. 74, No. 15, pp. 6748-6759.*

(Continued)

*Primary Examiner*—Bruce R. Campell
*Assistant Examiner*—Bao Qun Li
(74) *Attorney, Agent, or Firm*—Knobbe Martens Olson & Bear LLP

(57) ABSTRACT

The present invention relates to compositions and methods for enhancing the effect of vaccines in animals, such as domestic, sport, or pet species, and humans. More particularly, the use of Ribavirin as an adjuvant to a vaccine protocol and compositions having Ribavirin and an antigen are described.

52 Claims, 3 Drawing Sheets

U.S. PATENT DOCUMENTS

| | | | |
|---|---|---|---|
| 6,060,068 A | 5/2000 | Doyle et al. |
| 6,063,380 A | 5/2000 | Chedid et al. |
| 6,063,772 A | 5/2000 | Tam |
| 6,071,693 A | 6/2000 | Cha et al. |
| 6,074,816 A | 6/2000 | Houghton et al. |
| 6,074,846 A | 6/2000 | Ralston et al. |
| 6,074,852 A | 6/2000 | Ralston et al. |
| 6,096,541 A | 8/2000 | Houghton et al. |
| 6,130,326 A | 10/2000 | Ramasamy et al. |
| 6,150,087 A | 11/2000 | Chien |
| 6,150,337 A | 11/2000 | Tam |
| 6,153,421 A | 11/2000 | Yanagi et al. |
| 6,171,782 B1 | 1/2001 | Houghton et al. |
| 6,190,864 B1 | 2/2001 | Cha et al. |
| 6,194,140 B1 | 2/2001 | Houghton et al. |
| 6,214,583 B1 | 4/2001 | Cha et al. |
| 6,235,888 B1 | 5/2001 | Pachuk et al. |
| 6,274,148 B1 | 8/2001 | Ralston et al. |
| 6,297,370 B1 | 10/2001 | Cha et al. |
| 6,303,292 B1 | 10/2001 | Weiner et al. |
| 6,312,889 B1 | 11/2001 | Houghton et al. |
| 6,514,731 B1 | 2/2003 | Valenzuela et al. |
| 6,541,011 B2 | 4/2003 | Punnonen et al. |
| 6,555,114 B1 | 4/2003 | Leroux-Roels et al. |
| 6,653,125 B2 | 11/2003 | Donnelly et al. |
| 2002/0004048 A1 | 1/2002 | Ralston et al. |
| 2002/0165172 A1 | 11/2002 | Sallberg et al. |
| 2002/0183508 A1 | 12/2002 | Maertens et al. |
| 2002/0187945 A1 | 12/2002 | Tam |
| 2003/0007977 A1 | 1/2003 | Wheeler et al. |
| 2003/0008274 A1 | 1/2003 | Maertens et al. |
| 2003/0032005 A1 | 2/2003 | Maertens et al. |
| 2003/0044774 A1 | 3/2003 | Valenzuela et al. |
| 2003/0064360 A1 | 4/2003 | Maertens et al. |
| 2004/0092730 A1 | 5/2004 | Sallberg |

FOREIGN PATENT DOCUMENTS

| | | |
|---|---|---|
| EP | 0 414 475 | 2/1991 |
| EP | 0 450 931 | 6/1996 |
| EP | 0 543 924 | 6/1997 |
| EP | 0 842 947 | 5/1998 |
| EP | 0 693 687 | 7/1999 |
| EP | 0 556 292 | 12/1999 |
| EP | 1 034 785 | 9/2000 |
| EP | 0 318 216 | 8/2001 |
| WO | WO90/15070 | 12/1990 |
| WO | WO91/15575 | 10/1991 |
| WO | WO92/10092 | 6/1992 |
| WO | WO92/19743 | 11/1992 |
| WO | WO93/00365 | 1/1993 |
| WO | WO93/06126 | 4/1993 |
| WO | WO94/11530 | 5/1994 |
| WO | WO94/12305 | 6/1994 |
| WO | WO94/16737 | 8/1994 |
| WO | WO95/11995 | 5/1995 |
| WO | WO96/09805 | 4/1996 |
| WO | WO96/28162 | 9/1996 |
| WO | WO96/33739 | 10/1996 |
| WO | WO97/12043 | 4/1997 |
| WO | WO97/26883 | 7/1997 |
| WO | WO97/29212 | 8/1997 |
| WO | WO97/31256 | 8/1997 |
| WO | WO97/47358 | 12/1997 |
| WO | WO98/16184 | 4/1998 |
| WO | WO98/16186 | 4/1998 |
| WO | WO98/30223 | 7/1998 |
| WO | WO98/34640 | 8/1998 |
| WO | WO98/37180 | 8/1998 |
| WO | WO99/04008 | 1/1999 |
| WO | WO99/28482 | 6/1999 |
| WO | WO 00/44388 | 8/2000 |
| WO | WO 01/38360 | 5/2001 |
| WO | WO 01/96875 | 12/2001 |
| WO | WO 03/031588 | 4/2003 |

OTHER PUBLICATIONS

Heagy et al. J. Clin. Invest. 1991, vol. 87, pp. 1916-1924.*

Hahm et al., "NS3-4A of Hepatitis C Virus is a Chymotrypsin-Like Protease," Journal of Virology, The American Society for Microbiology, 69(4):2534-2539 (1995).

AASLD Abstracts 940, "Hepatitis C Virus NS54 Sequence Confirugation does not Predict Response to Induction Interferon Plus Ribavirin," *Hepatology*, p. 394A (2000).

Abrignani et al., "Perspectives for a vaccine against hepatitis C virus," Journal of Hepatology, 31: (suppl. 1):259-263 (1999).

Bartenschlager et al., "Substrate Determination for Cleavage in cis and in trans by the Hepatitis C Virus NS3 Proteinase," *Journal of Virology*, pp. 196-205, (1995).

Chen et al., "Human and Murine Antibody Recognition is Focused on the ATPase/Helicase, but not the Protease Domain of the Hepatitis C Virus Nonstructural 3 Protein," *Hepatology*, 28(1):219-224 (1998).

Chen et al., "Detection of Hepatitis C Virus RNA in the Cell Fraction of Saliva Before and After Oral Surgery," *J. Med. Virol.*, 43:223-226 (1995).

Chiang et al., "Enhancement of hepatitis C virus core antigen-specific type 1 T helper cell response by ribavirin correlates with the increased level of IL-2," *Vaccine Strategies Against Microbial Pathogens*, 42.11-42.16, p. A949 (date unknown).

Cotonat et al., "Pilot Study of Combination Therapy with Ribavirin and Interferon Alfa for the Retreatment of Chronic Hepatitis B e Antibody-Positive Patients," *Hepatology*, 31(2):502-506 (2000).

Cramp et al., "Hepatitis C Virus-Specific T-Cell Reactivity During Intereron and Ribavirin Treatment in Chronic Hepatitis C," *Gastron. Enterol.*, 118:346-355 (2000).

Encke et al., "DNA Vaccines," *Intervirology*, 42:117-124, (1999).

Encke et al., "Genetic Immunization Generates Cellular and Humoral Immune Responses Against the Nonstructural Proteins of the Hepatitis C Virus in a Murine Model", *Journal of Immunology*, 161:4917-4923 (1998).

Diepolder et al., "Possible mechanism involving T-lymphocyte response to non-structural protein 3 in viral clearance in acute hepatitis C virus infection," *Lancet*, 346(8981):1006-1007.

Fang et al., "Ribavirin enhancement of hepatitis C virus core antigen-specific type 1 T helper cell response correlates with the increased IL-12 level," *Journal of Hepatology*, 33(5):791-798 (2000).

Forns et al., "Hepatitis C virus lacking the hypervariable region 1 of the second envelope proteins is infectious and causes acute resalving or persistent infection in chimpanzees," PNAS, vol. 97, No. 24, pp. 13318-113323, (2000).

Gordon et al., "Immune responses to hepatitis C virus structural and nonstructural proteins induced byplasmid DNA immunizations," *Journal of Infectious Diseases*, 181(1):42-50.

Grakoui et al., "A second hepatitis C virus-encoded proteinase," *Proc. Natl. Acad. Sci USA*, 90:10583-10587, (1993).

Hsu et al., "Prospects for a Hepatitis C Virus Vaccine", *Cline Liver Dis*, 3(4):901-915 (1999).

Huffman et al., "In vitro effect of 1-beta-D-ribofuranosyl-1,2,4-triazole-3-carboxamide (virazole, ICN 1229) on deoxyribonucleic acid and ribonucleic acid viruses," *Antimicrob. Agents. Chemother.*, 3(2):235 (1973).

Hultgren et al., *J. Gen. Virol.*, 79:2381-2391 (1998).

Jin et al., "Expression, isolation, and characterization of the hepatitis C virus ATPase/RNA Helicase," *Arch. Biochem. Bioplys.*, 323:47-53 (1995).

Kakumu et al., "Pilot Study of Ribavirin and Interferon- for Chronic Hepatitis B," *Hepatoloy*, 18(2):258-263 (1993).

Kato, "Genome of human hepatitis C virus (HCV): gene organization, sequence diversity, and variation," *Microb. Com. Genomics*, 5(3):129-151 (2000).

Kumar et al, "Sequence, expression and reconstitution of an HCV genome from a British isolate derived from a single blood donation," *Journal of Viral Hepatitis*, 7:459-465 (2000).

Kwong et al., "Hepatitis C virus NS3/4A protease," *Antiviral Res.*, 41(1):67-84 (1999).

Kwong et al., "Structure and function of hepatitis C virus NS3 helicase," *Curr. Top. Microbiol. Immunol.*, 242:171-196 (2000).

Lawrence et al., "Advances in the treatment of hepatitis C," *Adv. Intern. Med.*, 45:65-105 (2000).

Li et al., "Role of the guanosine triphosphatase Rac2 in T helper 1 cell differentiation," *Science*, 288:2219-2222 (2000).

Lohmann et al., "Replication of Subgenomic Hepatitis C Virus RNAs in a Hepatoma Cell Line," Science, 285:110-113, (1999).

Marquardt et al., "Ribavirin inhibits mast cell mediator release," *J. Pharmacol. Exp. Therapeutics*, 240(1):145-149 (1987).

Marshall et al., "Detection of HCV RNA by the asymmetric gap ligase chain reaction," *PCR Methods and Applications*, 4(2):80-84 (1994).

Memar O. et al., "Antiviral Agents in Dermatology; Current Status and Future Prospects," *Internation Journal of Dermatology*, 34(9):597-606 (1995).

Missale et al., "Different clinical behaviours of acute hepatitis C virus infection are associated with different vigor of the anti-viral cell-mediaated immune response," *J. Clin. Invest.*, 98(3):706-714 (1996).

Neuberger et al., "Recombinant antibodies possessing novel effector functions," *Nature*, 312:604-608 (1984).

Pape et al., "Role of the specific T-cell response for clearance and control of hepatitis C virus," *J. Viral. Hepat.*, Supp. 6, 1:36-40 (1999).

Peavy et al., "Inhibition of murine plaque-forming cell responses in vivo by ribavirin," *J. Immunology*, 126(3):861-864 (1981).

Powers et al., "Selective inhibition of functional lymphocyte subpopulations by ribavirin," *Antimicrob. Agents. Chemother.*, 22(1):108-114 (1982).

Proust B. et al., "Two Successive Hepatitis C Virus Infections in an Intravenous Drug User," *Journal of Clinical Microbiology*, 38(8):3125-3127 (2000).

Ramasamy et al., "Monocyclic L-Nucleosides with Type 1 Cytokine-Inducing Activity," *Journal of Medicinal Chemistry*, 43(5):1019-1028 (2000).

Sällberg et al., "Characterization of humoral and CD4+ cellular responses after genetic immunization with retroviral vectors expressing different forms of the hepatitis B virus core and e antigens," *Journal of Virology*, 71:5295-5303 (1997).

Sällberg and Hultgren, "Vaccines Containing Ribavirin and Methods of use Thereof," U.S. Appl. No. 09/929,955, filed Aug. 15, 2001.

Salberg, "A Hepatitis C Virus Non-Structural NS3/4A Fusion Gene,"U.S. Appl. No. 09/930,591, filed Aug. 15, 2001.

Sällberg and Hultgren, "Vaccines Containing Ribavirin and Methods of use Thereof," U.S. Appl. No. 10/104,966, filed Mar. 22, 2002.

Schulof R. S., "Clinical, Virologic, and Immunologic Effects of Combination Therapy with Ribavirin and Isoprinosine in HIV-Infected Homosexual Men," *Journal of Acquired Immune Deficiency Syndromes*, 3(5):485-492 (1990).

Sidwell et al., "Broad-spectrum antiviral activity of Virazole: 1-beta-D-ribofuranosyl-1,2,4-triazole-3-carboxamide," *Science*, 177(50):705-706 (1972).

Smith et al., "Molecular Engineering of the *Autographa californica* Nuclear Polyhedrosis Virus Genome: Deletion Mutations Within the Polyhedrin Gene," *Journal of Virology*, 46:584 (1983).

Spector et al., "The Antviral Effect of Zidovudine and Ribavirin in Clinical Trials and the Use of p24 Antigen Levels as a Virologic Marker," *Journal of Infectious Diseases*, 159(5):822-828 (1989).

Szybalska and Szyvbalska, "Genetics of Human Cell Lines, IV, DNA-Mediated Heritable Transformationof a Biochemical Trait," *Proc Natl Acad Sci USA*, 48:2026 (1962).

Takeda et al., "Construction of chimaeric processed immunoglobulin genes containing mouse variable and human constant region sequences," *Nature*, 314:452-454 (1985).

Tam et al., "The Immunomodulatory effects of ribavirin: Recent findings," *International Antiviral News*, 7/6:99-100 (1999) (ABSTRACT).

Tam et al., "Ribavirin Polarizes Human T Cell Responses Towards a Type 1 Cyctokine Profile," *Journal of Hepatology*, 30(3):376-382 (1999).

Tan et al., "How hepatitis C virus counteracts the interferon response: the jury is still out on NS5A," *Virology*, 284(1):1-12 (2001).

Vaitukaitis et al., "A method for producing specific antisera with small doses of immunogen," *J. Clin. Endocrinology Metab.*, 33(6):988-991 (1971).

Walsh et al., "Update on chronic viral hepatitis", *Postgrad Medical Journal*, 77(910):498-505 (2001).

Wang et al., "Synthesis and Cytokine Modulation Properties of Pyrrolo[2,3,-d]-4-pyrimidone Nucleosides," *J. Med. Chem.*, 43(13):2566-2574 (2000).

Zhang et al., "Characterization of a monoclonal antibody and its singl-chain antibody fragment recognizing the nucleoside triphosphatase/helicase domain of the hepatitis C virus nonstructural 3 protein," *Clin. Diagn. Lab. Immunol.*, 7(1):58-63 (2000).

Zhang et al., "Interferon-α Treatment Induces Delayed CD4 Proliferate Responses to the Hepatitis C Virus Nonstructural Protein 3 Regardless of the Outcome of Therapy," *The Journal of Infectious Diseases*, 175:1294-1301 (1997).

Zhang et al., "Molecular basis for antibody cross-reactivity between the hepatitis C virs core protein and the hos-derived GOR protein," *Clin. Exp. Immunol.*, 96(3):403-409 (1994).

http://www.msi.com/life/products/cerius2/modules/analogbuilder.html, C2Analog Builder, Jul. 6, 2000.

U.S. Appl. No. 08/008,342, filed Jan. 26, 1993, Weiner et al.

U.S. Appl. No. 08/029,336, Mar. 11, 1993, Weiner et al.

Andre et al., "Increased Immune Response Elicited by DNA Vaccination with a Synthetic gp120 Sequence with Optimized Codon Usage," Journal of Virology, 72(2):1497-1503 (1998).

Bitter et al., *Methods in Enzymol.*, 153:516-544 (1987).

BLASTN 2.2.9., May 1, 2004.

Chang et al., Aliment Pharmacol Ther. Sep. 2000; 16(9): 1623-1632.

Chiang et al., "Enhancement of hepatitis C virus core antigen-specific type 1 T helper cell response by ribavirin correlates with the increased level of IL-2," Vaccine Strategies Against Microbial Pathogens, 42.11-42.16, p. A949 Apr. 20, 2000.

Colberre-Garapin, et al., "A new dominant hybrid selective marker for higher eukaryotic cells," *J. Mol. Biol.* 150:1 (1981).

Cote et al., "Generation of human monoclonal antibodies reactive with cellular antigens" *Proc. Natl. Acad. Sci.*, 80:2026-2030 (1983).

Database Genbank [Online] Dec. 2, 1994, retrieved from NCBI Database accession No. IO6434, XP002278035.

Database Registry [Online] No. 511600-20-7, XP02278058 abstract & WO 03/031588A, Apr. 17, 2003, Seq ID No. 1, 10 and 11 Claims.

Davis et al., *Human Gene Therapy*, 4(6):733 (1993).

Engvall, E., *Meth. Enzymol*, 70:419 (1980).

Fodor et al., *Science*, 251:767-773 (1991).

Heagy et al., J. Clin. Invest. 1991, vol. 87, pp. 1916-1924.

Hosoya et al., *J. INF. Dis.*, 168:641-646 (1993).

Houghten et al., *Proc. Natl. Acad. Sci. USA*, 82:51:32 (1985).

Hultgren et al., *Clin. Diagn. Lab. Immunol.* 4:630-632 (1997).

Huse W.D. et al. *Science* 256:1275-1281 (1989).

Hutchison et al., *Proc. Natl. Acad. Sci. USA* 253:6551 (1978).

Janknecht, et al., *Proc. Natl. Acad. Sci. USA* 88:8972-8976 (1991).

Kozbor et al., *Immunol Today* 4:72 (1983).

Kumar et al., "Hepatitis C virus genomic RNA for polyprotein gene," Journal of Hepatology, 7:459-465 (2000).

Lazdina et al., "Humoral and CD4* T helper (th) cell response to the hepatitis C virus non-structural 3 (NS3) protein: NS3 primes TH 1-like responses more effectively as a DNA-Based immunogen than as a recombinant protein," Journal of General Virology, 82:1299-1308 (2001).

Lo, *Mol. Cell. Biol.* 3:1803-1814 (1983).

Logan & Shenk, *Proc. Natl. Acad. Sci. USA* 81:3655-3659 (1984).

Lowy, et al., *Cell* 22:817 (1980).

Morrison et al. *Proc. Natl. Acad. Sci. USA* 81:6851-6855 (1984).

Mulligan & Berg, *Proc. Natl. Acad. Sci. USA* 78:2072 (1981).

NCBI, Genbank, M32084, Hepatitis C Virus . . . [Gi:32987] Aug. 2, 1993.

O'Hare, et al., *Proc. Natl. Acad. Sci. USA* 78:1527 (1981).

Orlandi et al., Proc. Natl. Acad. Sci. 86: 3833-3837 (1989).

Rudikoff et al., Immunology 1982, vol. 79, pp. 1979-1983.

Ruther et al., *EMBO J.*, 2:1791 (1983).

Santerre et al., *Gene.* 30:147 (1984).

Steigerwald-Mullen et al., J. Virol. 2000, vol. 74, No. 15, pp. 6748-6759.

Thompson et al., *Cell* 56:313-321 (1989).

Townsend et al., *J. Virol.* 71:3365 (1997).

Van der Putten et al., *Proc. Natl. Acad. Sci.*, USA 82:6148-6152 (1985).

Wigler et al., Cell 11:223 (1977).

Wigler et al., *Proc. Natl. Acad. Sci. USA* 77:3567 (1980).

Winter G. and Milstein C; *Nature* 349:293-299 (1991).

\* cited by examiner

VACCINES CONTAINING RIBAVIRIN AND METHODS OF USE THEREOF

CROSS-REFERENCE TO RELATED APPLICATIONS

This application is a continuation of U.S. patent application Ser. No. 10/104,966 filed on Mar. 22, 2002, now issued as U.S. Pat. No. 6,680,059, which is a continuation of U.S. patent application Ser. No. 09/705,547 filed on Nov. 3, 2000, now abandoned, both of which claim the benefit of priority of U.S. provisional patent application No. 60/229,175, filed Aug. 29, 2000. The aforementioned applications are hereby expressly incorporated by reference in their entireties.

FIELD OF THE INVENTION

The present invention relates to compositions and methods for enhancing the effect of vaccines in animals, such as domestic, sport, or pet species, and humans. More particularly, preferred embodiments concern the use of Ribavirin as an adjuvant and compositions having Ribavirin and an antigen.

BACKGROUND OF THE INVENTION

The use of vaccines to prevent disease in humans, farm livestock, sports animals, and household pets is a common practice. Frequently, however, the antigen used in a vaccine is not sufficiently immunogenic to raise the antibody titre to levels that are sufficient to provide protection against subsequent challenge or to maintain the potential for mounting these levels over extended time periods. Further, many vaccines are altogether deficient in inducing cell-mediated immunity, which is a primary immune defense against bacterial and viral infection. A considerable amount of research is currently focussed on the development of more potent vaccines and ways to enhance the immunogenicity of antigen-containing preparations. (See e.g., U.S. Pat. Nos. 6,056,961; 6,060,068; 6,063,380; and Li et al., Science 288:2219-2222 (2000)).

Notorious among such "weak" vaccines are hepatitis B vaccines. For example, recombinant vaccines against hepatitis B virus such as Genhevacb (Pasteur Merieux Serums et Vaccines, 58, Avenue Leclerc 69007 Lyon, France), Engerixb (Smith, Kline and Symbol French), and Recombivaxhb (Merck, Sharp, and Dhome) are effective only after at least three injections at 0, 30, and 60 or 180 days, followed by an obligatory booster after one year. (Chedid et al., U.S. Pat. No. 6,063,380). Additionally, many subjects receiving these vaccines respond poorly, if at all. Because many regions of the world are endemic for HBV infection, the poorly immunogenic character of existing HBV vaccines has become an extremely serious problem.

To obtain a stronger, humoral and/or cellular response, it is common to administer a vaccine in a material that enhances the immune response of the patient to the antigen present in the vaccine. The most commonly used adjuvants for vaccine protocols are oil preparations and alum. (Chedid et al., U.S. Pat. No. 6,063,380). A greater repertoire of safe and effective adjuvants is needed.

Nucleoside analogs have been widely used in anti-viral therapies due to their capacity to reduce viral replication. (Hosoya et al., J. Inf. Dis., 168:641-646 (1993)). Ribavirin (1-β-D-ribofuranosyl-1,2,4-triazole-3-carboxamide) is a synthetic guanosine analog that has been used to inhibit RNA and DNA virus replication. (Huffman et al., Antimicrob. Agents. Chemother., 3:235 (1973); Sidwell et al., Science, 177:705 (1972)). Ribavirin has been shown to be a competitive inhibitor of inositol mono-phosphate (IMP) dehydrogenase (IMPDH), which converts IMP to IMX (which is then converted to GMP). De Clercq, Anti viral Agents: characteristic activity spectrum depending on the molecular target with which they interact, Academic press, Inc., New York N.Y., pp. 1-55 (1993). Intracellular pools of GTP become depleted as a result of long term Ribavirin treatment.

In addition to antiviral activity, investigators have observed that a few guanosine analogs have an effect on the immune system. (U.S. Pat. Nos. 6,063,772 and 4,950,647). Ribavirin has been shown to inhibit functional humoral immune responses (Peavy et al., J. Immunol., 126:861-864 (1981); Powers et al., Antimicrob. Agents. Chemother., 22:108-114 (1982)) and IgE-mediated modulation of mast cell secretion. (Marquardt et al., J. Pharmacol. Exp. Therapeutics, 240:145-149 (1987)). Some investigators report that a daily oral therapy of Ribavirin has an immune modulating effect on humans and mice. (Hultgren et al., J. Gen. Virol., 79:2381-2391 (1998) and Cramp et al., Gastron. Enterol., 118:346-355 (2000)). Nevertheless, the current understanding of the effects of Ribavirin on the immune system is in its infancy.

SUMMARY OF THE INVENTION

It has been discovered that Ribavirin can be used as an adjuvant to enhance an immune response to an antigen. Embodiments described herein include "strong" vaccine preparations that comprise an antigen and Ribavirin. Generally, these preparations have an amount of Ribavirin that is sufficient to enhance an immune response to the antigen. Other aspects of the invention include methods of enhancing the immune response of an animal, including a human, to an antigen. By one approach, for example, an animal in need of a potent immune response to an antigen is identified and then is provided an amount of Ribavirin together with the antigen that is effective to enhance an immune response in the animal. In some methods, the Ribavirin and the antigen are provided in combination and in others, the Ribavirin and the antigen are provided separately. Thus, several embodiments concern the manufacture and use of vaccine preparations having Ribavirin and an antigen.

Preferred vaccine compositions comprise Ribavirin and a hepatitis viral antigen. The antigen can be a peptide or nucleic acid-based (e.g., a RNA encoding a peptide antigen or a construct that expresses a peptide antigen when introduced to a subject). HBV antigens that are suitable include, for example, hepatitis B surface antigen (HBsAg), hepatitis core antigen (HBcAg), hepatitis e antigen (HBeAg), and nucleic acids encoding these molecules. Compositions having Ribavirin and an antigen from the hepatitis A virus (HAV) or Ribavirin and a nucleic acid encoding an antigen from HAV are also embodiments. Still further, compositions having Ribavirin and an antigen from the hepatitis C virus (HCV) or Ribavirin and a nucleic acid encoding an antigen from HCV are embodiments.

Furthermore, compositions having a mixture of the antigens above are embodiments of the present invention. For example, some compositions comprise a HBV antigen, a HAV antigen, and Ribavirin or a HBV antigen, a HCV antigen, and Ribavirin or a HAV antigen, a HCV antigen, and Ribavirin or a HBV antigen, a HAV antigen, a HCV antigen, and Ribavirin. Other embodiments comprise Ribavirin and a nucleic acid encoding a mixture of the antigens described above. Some embodiments also include other adjuvants, binders, emulsifiers, carriers, and fillers, as known in the art, including, but not limited to, alum, oil, and other compounds that enhance an immune response.

Preferred methods involve providing an animal in need with a sufficient amount of Ribavirin and a hepatitis viral antigen (e.g., HBV antigen, HAV antigen, HCV antigen a nucleic acid encoding one of these antigens or any combination thereof). Accordingly, one embodiment includes identifying an animal in need of an enhanced immune response to a hepatitis viral antigen (e.g., an animal at risk or already infected with a hepatitis infection) and providing to said animal an amount of Ribavirin that is effective to enhance an immune response to the hepatitis viral antigen.

DETAILED DESCRIPTION OF THE INVENTION

Figure 1:
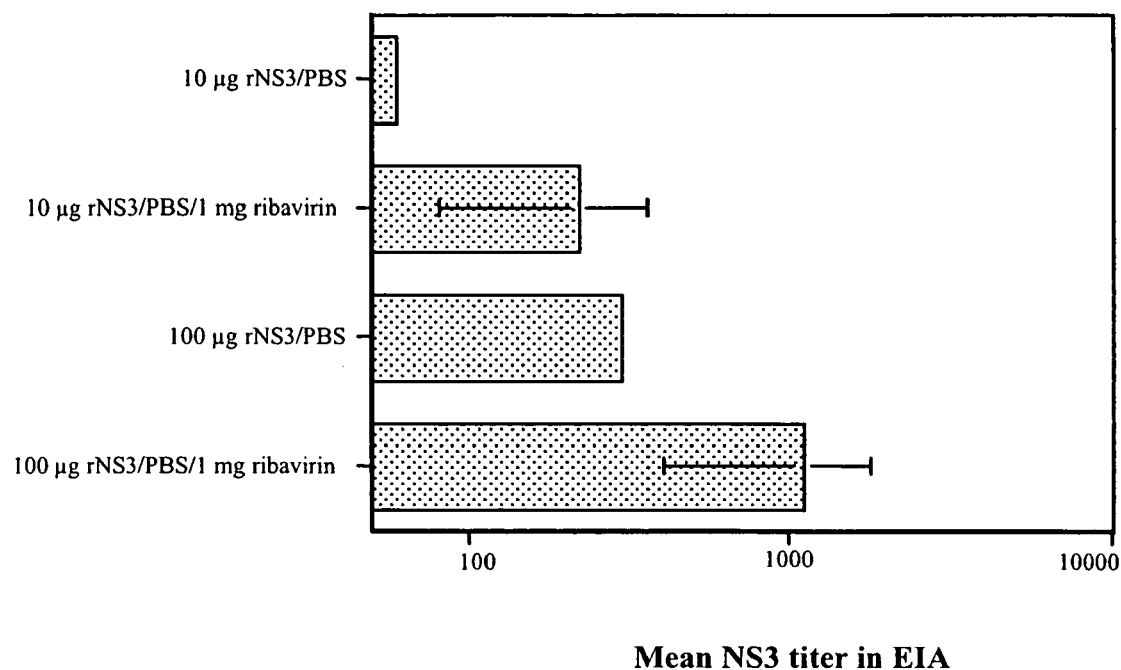
FIG. 1 is a graph showing the humoral response to 10 and 100 μg recombinant Hepatitis C virus (HCV) non structural 3 protein (NS3), as determined by mean end point titres, when a single dose of 1 mg of Ribavirin was co-administered.

It has been discovered that compositions comprising Ribavirin and an antigen can boost an animal's immune response to the antigen. That is, Ribavirin can be used as an "adjuvant," which for the purposes of this disclosure, refers to a compound that has the ability to enhance the immune response to a particular antigen. Such adjuvant activity is manifested by a significant increase in immune-mediated protection against the antigen, and was demonstrated by an increase in the titer of antibody raised to the antigen and an increase in proliferative T cell responses.

Several vaccine preparations that comprise Ribavirin and an antigen are described herein. Vaccine formulations containing Ribavirin can vary according to the amount of Ribavirin, the form of Ribavirin, and the type of antigen. The antigen can be a peptide or a nucleic acid (e.g., a RNA encoding a peptide antigen or a construct that expresses a peptide antigen when introduced into a subject). Preferred vaccine formulations comprise Ribavirin and a hepatitis viral antigen (e.g., HBV antigen, HAV antigen, HCV antigen, a nucleic acid encoding these molecules, or any combination thereof).

Methods of enhancing the immune response of an animal, including humans, to an antigen are also described herein. One method, for example, involves identifying an animal in need of an enhanced immune response to an antigen and providing the animal the antigen and an amount of Ribavirin that is effective to enhance an immune response to the antigen. Preferred methods involve providing the animal in need with Ribavirin and a hepatitis antigen (e.g., HBV antigen, HAV antigen, HCV antigen, a nucleic acid encoding these molecules, or any combination thereof). The section below describes the manufacture of vaccines having Ribavirin and an antigen in greater detail.

Vaccines Containing Ribavirin

The vaccines comprise Ribavirin and an antigen and may contain other ingredients including, but not limited to, adjuvants, binding agents, excipients such as stabilizers (to promote long term storage), emulsifiers, thickening agents, salts, preservatives, solvents, dispersion media, coatings, antibacterial and antifungal agents, isotonic and absorption delaying agents and the like. These vaccine preparations are suitable for treatment of animals either as a preventive measure to avoid a disease or condition or as a therapeutic to treat animals already afflicted with a disease or condition.

The vaccine compositions can be manufactured in accordance with conventional methods of galenic pharmacy to produce medicinal agents for administration to animals, e.g., mammals including humans. Ribavirin can be obtained from commercial suppliers (e.g., Sigma and ICN). Ribavirin and/or the antigen can be formulated into the vaccine with and without modification. For example, the Ribavirin and/or antigen can be modified or derivatized to make a more stable molecule and/or a more potent adjuvant. By one approach, the stability of Ribavirin and/or an antigen can be enhanced by coupling the molecules to a support such as a hydrophilic polymer (e.g., polyethylene glycol).

Many more Ribavirin derivatives can be generated using conventional techniques in rational drug design and combinatorial chemistry. For example, Molecular Simulations Inc. (MSI), as well as many other suppliers, provide software that allows one of skill to build a combinatorial library of organic molecules. The C2.Analog Builder program, for example, can be integrated with MSI's suite of Cerius2 molecular diversity software to develop a library of Ribavirin derivatives that can be used with the embodiments described herein.

By one approach, the chemical structure of Ribavirin is recorded on a computer readable media and is accessed by one or more modeling software application programs. The C2.Analog Builder program in conjunction with C2Diversity program allows the user to generate a very large virtual library based on the diversity of R-groups for each substituent position, for example. Compounds having the same structure as the modeled Ribavirin derivatives created in the virtual library are then made using conventional chemistry or can be obtained from a commercial source.

The newly manufactured Ribavirin derivatives are then screened in characterization assays, which determine the extent of adjuvant activity of the molecule and/or the extent of its ability to modulate of an immune response. Some characterization assays may involve virtual drug screening software, such as C2.Ludi. C2.Ludi is a software program that allows a user to explore databases of molecules (e.g., Ribavirin derivatives) for their ability to interact with the active site of a protein of interest (e.g., RAC2 or another GTP binding protein). Based upon predicted interactions discovered with the virtual drug screening software, the Ribavirin derivatives can be prioritized for further characterization in conventional assays that determine adjuvant activity and/or the extent of a molecule to modulate an immune response.

Example 1 describes a characterization assay that was used to evaluate the adjuvant activity of Ribavirin.

EXAMPLE 1

This characterization assay can be used with any Ribavirin derivative or combinations of Ribavirin derivatives to determine the extent of adjuvant activity of the particular vaccine formulation. Accordingly, groups of three to five Balb/c mice (BK Universal, Uppsala, Sweden) were immunized i.p or s.c. (e.g., at the base of the tail) with 10 μg or 100 μg of recombinant hepatitis C virus non-structural 3 (NS3) protein. The rNS3 was dissolved in phosphate buffered saline (PBS) alone or PBS containing 1 mg Ribavirin (obtained from ICN, Costa Mesa, Calif.). Mice were injected with a total volume of 100 μl per injection.

At two and four weeks following ip. immunization, all mice were bled by retro-orbital sampling. Serum samples were collected and analyzed for the presence of antibodies to rNS3. To determine the antibody titer, an enzyme immunoassay (EIA) was performed. (See e.g., Hultgren et al., *J Gen Virol.* 79:2381-91 (1998) and Hultgren et al., *Clin. Diagn. Lab. Immunol.* 4:630-632 (1997), both of which are herein expressly incorporated by reference in their entireties). The antibody levels were recorded as the highest serum dilution giving an optical density at 405 nm more than twice that of non-immunized mice.

Mice that received 10 μg or 100 μg rNS3 mixed with 1 mg Ribavirin in PBS displayed consistently higher levels of NS3 antibodies. The antibody titer that was detected by EIA at two weeks post-immunization is shown in FIG. 1. The vaccine formulations having 1 mg of Ribavirin and either 10 μg or 100 μg of rNS3 induced a significantly greater antibody titer than the vaccine formulations composed of only rNS3. This data provides evidence that Ribavirin has an adjuvant effect on the humoral immune response of an animal and thus, enhances the immune response to the antigen.

The example below describes experiments that were performed to determine the amount of Ribavirin that was needed to elicit an adjuvant effect.

EXAMPLE 2

Figure 2:
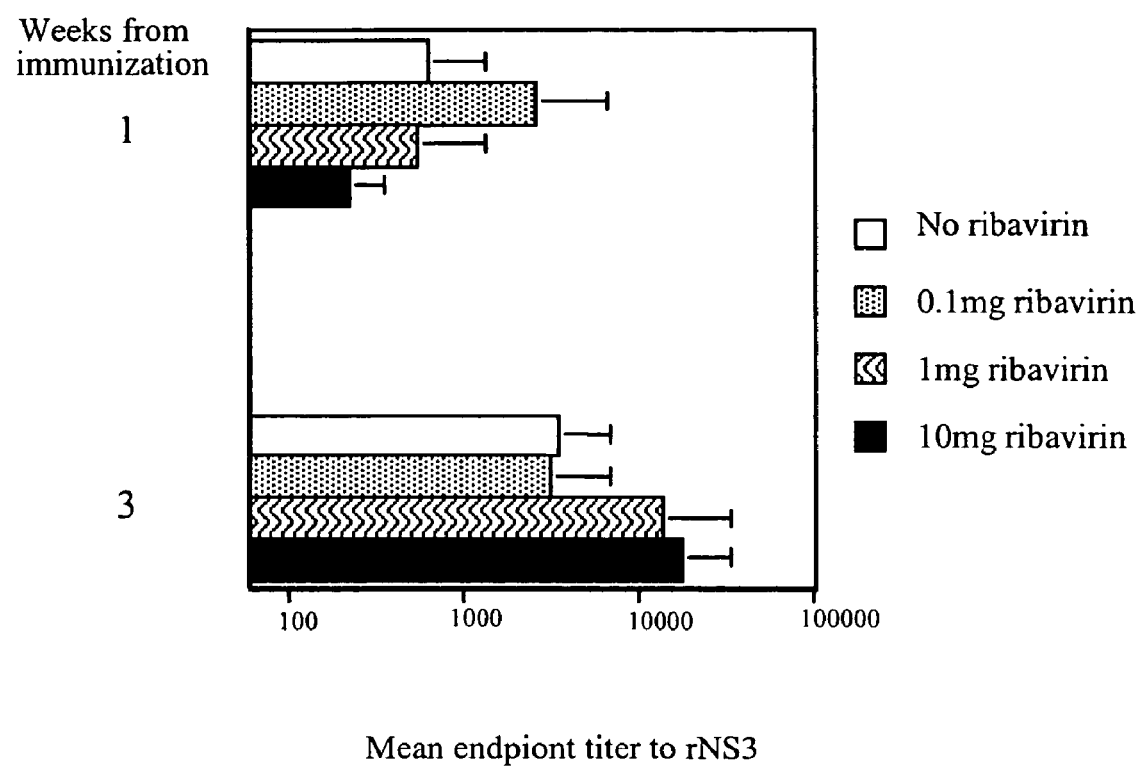
FIG. 2 is a graph showing the humoral response to 20 μg recombinant Hepatitis C virus (HCV) non structural 3 protein (NS3), as determined by mean end point titres, when a single dose of 0.1, 1.0, or 10 mg of Ribavirin was co-administered.

To determine the dose of Ribavirin that is required to provide an adjuvant effect, the following experiments were performed. Groups of mice (three per group) were immunized with a 20 μg rNS3 alone or a mixture of 20 μg rNS3 and 0.1 mg, 1 mg, or 10 mg Ribavirin. The levels of antibody to the antigen were then determined by EIA. The mean endpoint titers at weeks 1 and 3 were plotted and are shown in FIG. 2. It was discovered that the adjuvant effect provided by Ribavirin had different kinetics depending on the dose of Ribavirin provided. For example, low doses (<1 mg) of Ribavirin were found to enhance antibody levels at week one but not at week three, whereas, higher doses (1-10 mg) were found to enhance antibody levels at week three. These data further verify that Ribavirin can be administered as an adjuvant and establish that that the dose of Ribavirin can modulate the kinetics of the adjuvant effect.

The example below describes another characterization assay that was performed to evaluate the ability of Ribavirin to modulate a cellular immune response.

EXAMPLE 3

This characterization assay can be used with any Ribavirin derivative or combinations of Ribavirin derivatives to determine the extent that a particular vaccine formulation modulates a cellular immune response. To determine $CD4^+$ T cell responses to Ribavirin-containing vaccine, groups of mice were immunized s.c. with either 100 μg rNS3 in PBS or 100 μg rNS3 and 1 mg Ribavirin in PBS. The mice were sacrificed ten days post-immunization and their lymph nodes were harvested and drained. In vitro recall assays were then performed. (See e.g., Hultgren et al., *J Gen Virol.* 79:2381-91 (1998) and Hultgren et al., *Clin. Diagn. Lab. Immunol.* 4:630-632 (1997), both of which are herein expressly incorporated by reference in their entireties). The amount of $CD4^+$ T cell proliferation was determined at 96 h of culture by the incorporation of [$^3$H] thymidine.

Figure 3:
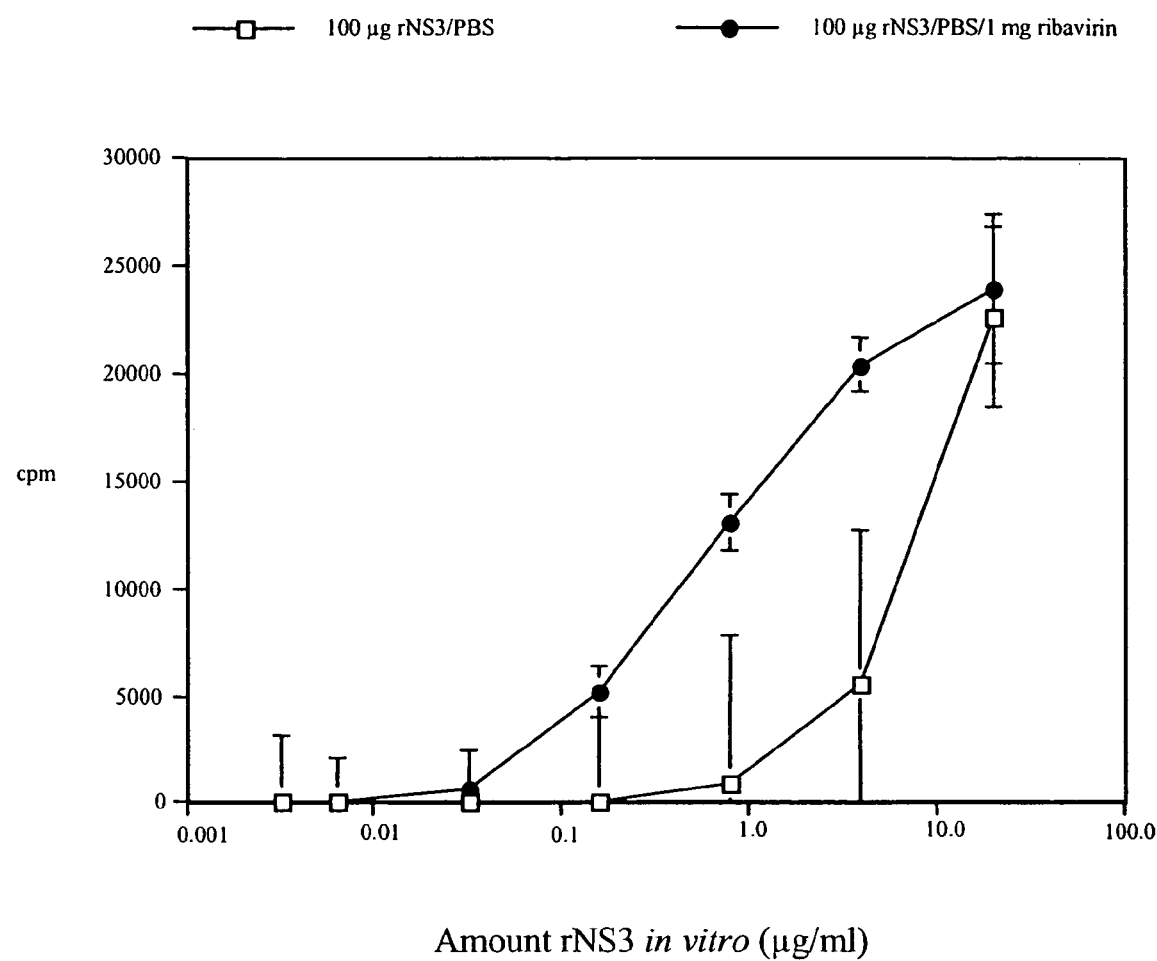
FIG. 3 is a graph showing the effects of a single dose of 1 mg Ribavirin on NS3-specific lymph node proliferative responses, as determined by in vitro recall responses.

As shown in FIG. 3, mice that were immunized with 100 μg rNS3 mixed with 1 mg Ribavirin had a much greater T cell proliferative response than mice that were immunized with 100 μg rNS3 in PBS. This data provides evidence that Ribavirin can enhance a cellular immune response (e.g., by promoting the effective priming of T cells).

The example below describes the use of Ribavirin in conjunction with a commercial vaccine preparation.

EXAMPLE 4

The adjuvant effect of Ribavirin was also tested when mixed with two doses of a commercially available vaccine containing HBsAg and alum. (Engerix, SKB). Approximately 0.2 μg or 2 μg of Engerix vaccine was mixed with either PBS or 1 mg Ribavirin in PBS and the mixtures were injected intra peritoneally into groups of mice (three per group). A booster containing the same mixture was given on week four and all mice were bled on week six. The serum samples were diluted from 1:60 to 1:37500 and the dilutions were tested by EIA, as described above, except that purified human HBsAg (kindly provided by Professor DL Peterson, Commonwealth University, Va.) was used as the solid phase antigen. As shown in TABLE 1, vaccine formulations having Ribavirin enhanced the response to 2 μg of an existing vaccine despite the fact that the vaccine already contained alum. That is, by adding Ribavirin to a suboptimal vaccine dose (i.e., one that does not induce detectable antibodies alone) antibodies became detectable, providing evidence that the addition of Ribavirin allows for the use of lower antigen amounts in a vaccine formulation without compromising the immune response.

TABLE 1

| | End point antibody titer to HBsAg in EIA | | | | | | | | | | | |
|---|---|---|---|---|---|---|---|---|---|---|---|---|
| | 0.02 μg Engerix | | | | | | 0.2 μg Engerix | | | | | |
| | No Ribavirin | | | 1 mg Ribavirin | | | No Ribavirin | | | 1 mg Ribavirin | | |
| Week | #1 | #2 | #3 | #1 | #2 | #3 | #1 | #2 | #3 | #1 | #2 | #3 |
| 6 | <60 | <60 | <60 | <60 | <60 | <60 | <60 | <60 | <60 | 300 | 60 | <60 |

Any antigen that can be used to generate an immune response in an animal can be combined with Ribavirin so as to prepare the vaccines described herein. That is, antigens that can be incorporated into such a vaccine comprise bacterial antigens, fungal antigens, plant antigens, mold antigens, viral antigens, cancer cell antigens, toxin antigens, chemical antigens, and self-antigens. Although many of these antigens are molecules that induce a significant immune response without an adjuvant, Ribavirin can be administered in conjunction with or combined with "strong" or "weak" antigens to enhance the immune response. In addition, the use of Ribavirin as an adjuvant may allow for the use of lower amounts of vaccine antigens while retaining immunogenicity.

Preferred embodiments comprise Ribavirin and a viral antigen. Preferred viral antigens are hepatitis viral antigens. Vaccines can comprise, for example, Ribavirin and an HBV antigen, HAV antigen, HCV antigen or any combination of these antigens. Preferred viral antigens include hepatitis B surface antigen (HBsAg), hepatitis core antigen (HBcAg), and hepatitis E antigen (HBeAg).

For example, HCV vaccine embodiments comprise Ribavirin and a HCV peptide of at least 3 consecutive amino acids of SEQ. ID. No.: 1. That is, a vaccine embodiment can have Ribavirin and a HCV peptide with a length of at least 3-10 consecutive amino acids, 10-50 consecutive amino acids, 50-100 consecutive amino acids, 100-200 consecutive amino acids, 200-400 consecutive amino acids, 400-800 consecutive amino acids, 800-1200 consecutive amino acids, 1200-1600 consecutive amino acids, 1600-2000 consecutive amino acids, 2000-2500 consecutive amino acids, and 2500-3011 consecutive amino acids of SEQ ID. No. 1. Preferred HCV vaccines comprise Ribavirin and a peptide of at least 3 consecutive amino acids of HCV core protein (SEQ. ID. No. 2), HCV E1 protein (SEQ. ID. No. 3), HCV E2 protein (SEQ. ID. No. 4), HCV NS2 (SEQ. ID. No. 5), HCV NS3 (SEQ. ID. No. 6), HCV NS4A (SEQ. ID. No. 7), HCV NS4B (SEQ. ID. No. 8), or HCV NS5A/B (SEQ. ID. No. 9). That is, preferred HCV vaccines can comprise Ribavirin and a peptide with a length of at least 3-10 consecutive amino acids, 10-50 consecutive amino acids, 50-100 consecutive amino acids, 100-200 consecutive amino acids, 200-400 consecutive amino acids, 400-800 consecutive amino acids, and 800-1040 consecutive amino acids of any one of (SEQ. ID. Nos. 2-9).

Similarly, preferred HBV vaccine embodiments comprise Ribavirin and a HBV peptide of at least 3 consecutive amino acids of HBsAg (SEQ. ID. No.: 10) or HBcAg and HBeAg (SEQ. ID. No. 11). That is, a vaccine embodiment can have Ribavirin and a HBV peptide with a length of at least 3-10 consecutive amino acids, 10-50 consecutive amino acids, 50-100 consecutive amino acids, 100-150 consecutive amino acids, 150-200 consecutive amino acids, and 200-226 consecutive amino acids of either SEQ. ID. No. 10 or SEQ. ID. No. 11. Further, preferred HAV embodiments comprise Ribavirin and a HAV peptide with a length of at least 3-10 consecutive amino acids, 10-50 consecutive amino acids, 50-100 consecutive amino acids, 100-200 consecutive amino acids, 200-400 consecutive amino acids, 400-800 consecutive amino acids, 800-1200 consecutive amino acids, 1200-1600 consecutive amino acids, 1600-2000 consecutive amino acids, and 2000-2227 consecutive amino acids of SEQ ID. No. 12.

In addition to peptide antigens, nucleic acid-based antigens can be used in the vaccine compositions described herein. Various nucleic acid-based vaccines are known and it is contemplated that these compositions and approaches to immunotherapy can be augmented by introducing Ribavirin (See e.g., U.S. Pat. No. 5,589,466, herein expressly incorporated by reference in its entirety).

By one approach, for example, a gene encoding a polypeptide antigen of interest is cloned into an expression vector capable of expressing the polypeptide when introduced into a subject. The expression construct is introduced into the subject in a mixture of Ribavirin or in conjunction with Ribavirin (e.g., Ribavirin is administered shortly after the expression construct at the same site). Alternatively, RNA encoding a polypeptide antigen of interest is provided to the subject in a mixture with Ribavirin or in conjunction with Ribavirin. Where the polynucleotide is to be DNA, promoters suitable for use in various vertebrate systems are well known. For example, for use in murine systems, suitable strong promoters include RSV LTR, MPSV LTR, SV40 IEP, and metallothionein promoter. In humans, on the other hand, promoters such as CMV IEP can be used. All forms of DNA, whether replicating or non-replicating, which do not become integrated into the genome, and which are expressible, can be used.

Preferred nucleic acid-based antigens include a nucleotide sequence of at least 9 consecutive nucleotides of HCV (SEQ. ID. No. 13), HBV (SEQ. ID. No.:14), or HAV (SEQ. ID. No. 15). That is, a nucleic acid based antigen can comprise at least 9-25 consecutive nucleotides, 25-50 consecutive nucleotides, 50-100 consecutive nucleotides, 100-200 consecutive nucleotides, 200-500 consecutive nucleotides, 500-1000 consecutive nucleotides, 1000-2000 consecutive nucleotides, 2000-4000 consecutive nucleotides, 4000-8000 consecutive nucleotides, and 8000-9416 consecutive nucleotides of any one of SEQ. ID. Nos.: 13-15 or an RNA that corresponds to these sequences.

The example below describes one approach for using a nucleic acid-based antigen in conjunction with Ribavirin.

EXAMPLE 5

The following describes an approach to immunize an animal with a vaccine comprising a nucleic acid-based antigen and Ribavirin. Five to six week old female and male Balb/C mice are anesthetized by intraperitoneal injection with 0.3 ml of 2.5% Avertin. A 1.5 cm incision is made on the anterior thigh, and the quadriceps muscle is directly visualized. One group of mice are injected with approximately 20 µg of an expression construct having the gp-120 gene, driven by a cytomegalovirus (CMV) promotor and second group of mice are injected with approximately 5 µg of capped in vitro transcribed RNA (e.g., SP6, T7, or T3 (Ambion)) encoding gp-120. These two groups are controls. A third group of mice is injected with approximately 20 µg of the expression vector having the gp-120 gene and the CMV promoter mixed with 1 mg of Ribavirin and a fourth group of mice is injected with approximately 5 µg of capped in vitro transcribed RNA mixed with 1 mg Rbavirin. The vaccines are injected in 0.1 ml of solution (PBS) in a 1 cc syringe through a 27 gauge needle over one minute, approximately 0.5 cm from the distal insertion site of the muscle into the knee and about 0.2 cm deep. A suture is placed over the injection site for future localization, and the skin is then closed with stainless steel clips.

Blood samples are obtained prior to the injection (Day 0) and up to more than 40 days post injection. The serum from each sample is serially diluted and assayed in a standard ELISA technique assay for the detection of antibody, using recombinant gp-120 protein made in yeast as the antigen. Both IgG and IgM antibodies specific for gp-120 will be detected in all samples, however, groups three and four, which contained the Ribavirin, will exhibit a greater immune response to the gp-120 as measured by the amount and/or titer of antibody detected in the sera.

Many other ingredients can be present in the vaccine. For example, the Ribavirin and antigen can be employed in admixture with conventional excipients (e.g., pharmaceutically acceptable organic or inorganic carrier substances suitable for parenteral, enteral (e.g., oral) or topical application that do not deleteriously react with the Ribavirin and/or antigen). Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more suitable carriers are described in *Remmington's* Pharmaceutical Sciences, 15th Edition, Easton:Mack Publishing Company, pages 1405-1412 and 1461-1487(1975) and The National *Formulary* XIV, 14th Edition, Washington, American Pharmaceutical Association (1975), herein expressly incorporated by reference in their entireties. Vaccines can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with Ribavirin or the antigen.

The effective dose and method of administration of a particular vaccine formulation can vary based on the individual patient and the type and stage of the disease, as well as other factors known to those of skill in the art. Therapeutic efficacy and toxicity of the vaccines can be determined by standard pharmaceutical procedures in cell cultures or experimental animals, e.g., ED50 (the dose therapeutically effective in 50% of the population). The data obtained from cell culture assays and animal studies can be used to formulate a range of dosage for human use. The dosage of the vaccines lies preferably within a range of circulating concentrations that include the ED50 with no toxicity. The dosage varies within this range depending upon the type of Ribavirin derivative and antigen, the dosage form employed, the sensitivity of the patient, and the route of administration.

Since Ribavirin has been on the market for several years, many dosage forms and routes of administration are known. All known dosage forms and routes of administration can be provided within the context of the embodiments described herein. Preferably, an amount of Ribavirin that is effective to enhance an immune response to an antigen in an animal can be considered to be an amount that is sufficient to achieve a blood serum level of antigen approximately 0.25-12.5 µg/ml in the animal, preferably, about 2.5 µg/ml. In some embodiments, the amount of Ribavirin is determined according to the body weight of the animal to be given the vaccine. Accordingly, the amount of Ribavirin in a vaccine formulation can be from about 0.1-6.0 mg/kg body weight. That is, some embodiments have an amount of Ribavirin that corresponds to approximately 0.1-1.0 mg/kg, 1.1-2.0 mg/kg, 2.1-3.0 mg/kg, 3.1-4.0 mg/kg, 4.1-5.0 mg/kg, 5.1, and 6.0 mg/kg body weight of an animal. More conventionally, the vaccines contain approximately 0.25 mg-2000 mg of Ribavirin. That is, some embodiments have approximately 250 µg, 500 µg, 1 mg, 25 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, and 2 g of Ribavirin.

Vaccines comprising various antigens and amounts of these antigens have been provided to animals for many years. Thus, conventional vaccine preparations can be modified by adding an amount of Ribavirin that is sufficient to enhance an immune response to the antigen. That is, existing conventional vaccine formulations can be modified by simply adding Ribavirin to the preparation or by administering the conventional vaccine in conjunction with Ribavirin (e.g., shortly before or after providing the antigen). As one of skill in the art will appreciate, the amount of antigens in a vaccine can vary depending on the type of antigen and its immunogenicity. The amount of antigens in the vaccines can vary accordingly. Nevertheless, as a general guide, the vaccines can have approximately 0.25 mg-2000 mg of an antigen (e.g., a hepatitis viral antigen).

In some approaches described herein, the exact amount of Ribavirin and/or antigen is chosen by the individual physician in view of the patient to be treated. Further, the amounts of Ribavirin can be added in combination to or separately from the same or equivalent amount of antigen and these amounts can be adjusted during a particular vaccination protocol so as to provide sufficient levels in light of patient-specific or antigen-specific considerations. In this vein, patient-specific and antigen-specific factors that can be taken into account include, but are not limited to, the severity of the disease state of the patient, age, and weight of the patient, diet, time and frequency of administration, drug combination(s), reaction sensitivities, and tolerance/response to therapy.

Routes of administration of the vaccines described herein include, but are not limited to, transdermal, parenteral, gastrointestinal, transbronchial, and transalveolar. Transdermal administration can be accomplished by application of a cream, rinse, gel, etc. capable of allowing Ribavirin and antigen to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having Ribavirin and an antigen that are suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein expressly incorporated by reference in its entirety.

Compositions having Ribavirin and an antigen that are suitable for parenteral administration include, but are not limited to, pharmaceutically acceptable sterile isotonic solutions. Such solutions include, but are not limited to, saline, phosphate buffered saline and oil preparations for injection into a central venous line, intravenous, intramuscular, intraperitoneal, intradermal, or subcutaneous injection.

Compositions having Ribavirin and an antigen that are suitable for transbronchial and transalveolar administration include, but not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver vaccines having Ribavirin and an antigen.

Compositions having Ribavirin and an antigen that are suitable for gastrointestinal administration include, but not limited to, pharmaceutically acceptable powders, pills or liquids for ingestion and suppositories for rectal administration.

Once the vaccine comprising Ribavirin and an antigen has been obtained, it can be administered to a subject in need to treat or prevent diseases. The next section describes methods that employ the vaccines described above.

Methods of Use of Vaccines that Contain Ribavirin

The vaccines containing Ribavirin and an antigen can be used to treat and prevent a vast spectrum of diseases and can enhance the immune response of an animal to an antigen. As one of skill in the art will appreciate conventional vaccines have been administered to subjects in need of treatment or prevention of bacterial diseases, viral diseases, fungal diseases, and cancer. Because the vaccines described herein include conventional vaccines, which have been modified by the addition of Ribavirin, the methods described herein include the treatment and prevention of a disease using a vaccine that comprises an antigen and Ribavirin.

Preferred embodiments concern methods of treating or preventing hepatitis infection. In these embodiments, an animal in need is provided a hepatitis antigen (e.g., a peptide antigen or nucleic acid-based antigen) and an amount of Ribavirin sufficient to exhibit an adjuvant activity in said animal. Accordingly, an animal can be identified as one in need by using currently available diagnostic testing or clinical evaluation. The range of hepatitis viral antigens that can be used with these embodiments is diverse. Preferred hepatitis viral antigens include an HBV antigen, an HAV antigen, an HCV antigen, nucleic acids encoding these antigens, or any combination thereof. Highly preferred embodiments include an HBV antigen selected from the group consisting of hepatitis B surface antigen (HBsAg), hepatitis core antigen (HBcAg), and hepatitis E antigen (HBeAg), in particular, the peptide and nucleic acid-based antigens describes supra. The Ribavirin and antigen can be provided separately or in combination, and other adjuvants (e.g., oil, alum, or other agents that enhance an immune response) can also be provided to the animal in need. Thus, preferred embodiments include methods of treating or preventing hepatitis in an animal (e.g., HBV) by identifying an infected animal or an animal at risk of infection and providing said animal a hepatitis antigen (e.g., HBsAg, HBcAg, and HBeAg) and an amount of Ribavirin sufficient to exhibit adjuvant activity.

Other embodiments include methods of enhancing an immune response to an antigen by providing an animal in need with an amount of Ribavirin that is effective to enhance said immune response. In these embodiments, an animal in need of an enhanced immune response to an antigen is identified by using currently available diagnostic testing or clinical evaluation. Oftentimes these individuals will be suffering from a disease (e.g., bacterial, fungal, mold, viral, or cancer) or are at risk from contracting the disease. However, an animal in need of an enhanced immune response can be an animal that has been poisoned (e.g., bit by a poisonous insect or animal) or that has been exposed to a toxin or other toxic compound. Once identified, these animals are provided an appropriate antigen and an amount of Ribavirin effective to enhance an immune response in the animal.

As above, the hepatitis viral antigens that can be used with these embodiments include, but are not limited to, an HBV antigen, an HAV antigen, an HCV antigen, a nucleic acid encoding these molecules, or any combination thereof. Highly preferred embodiments include an HBV antigen selected from the group consisting of hepatitis B surface antigen (HBsAg), hepatitis core antigen (HBcAg), and hepatitis E antigen (HBeAg), in particular, the peptide and nucleic acid-based antigens described supra. The Ribavirin and antigen can be provided separately or in combination, and other adjuvants (e.g., oil, alum, or other agents that enhance an immune response) can also be provided to the animal in need. Thus, preferred embodiments include methods of enhancing an immune response to a hepatitis antigen (e.g., HBV) by identifying an animal in need and providing the animal a hepatitis antigen (e.g., HBsAg, HBcAg, and HBeAg) and an amount of Ribavirin that is effective to enhance an immune response in the animal.

Although the invention has been described with reference to embodiments and examples, it should be understood that various modifications can be made without departing from the spirit of the invention. Accordingly, the invention is limited only by the following claims. All references cited herein are hereby expressly incorporated by reference.

5

26

What is claimed is:

1. A method of increasing the titer of hepatitis viral antigen-specific IgG antibodies in a subject in need thereof consisting essentially of providing, in a single administration, an immunogenic composition that comprises an effective amount of ribavirin and said hepatitis viral antigen to said subject.

2. The method of claim 1, further comprising identifying said subject as one in need of an increase in titer of IgG antibodies that are specific for said hepatitis viral antigen.

3. The method of claim 1, further comprising measuring the increase in the titer of hepatitis viral antigen-specific IgG antibodies in a subject.

4. The method of claim 2, further comprising measuring the increase in the titer of hepatitis viral antigen-specific IgG antibodies in said subject.

5. The method of claim 1, wherein said hepatitis antigen is an antigen from hepatitis B virus or hepatitis C virus.

6. The method of claim 2, wherein said hepatitis antigen is an antigen from hepatitis B virus or hepatitis C virus.

7. The method of claim 3, wherein said hepatitis antigen is an antigen from hepatitis B virus or hepatitis C virus.

8. The method of claim 4, wherein said hepatitis antigen is an antigen from hepatitis B virus or hepatitis C virus.

9. The method of claim 1, wherein said viral antigen comprises a hepatitis C viral antigen.

10. The method of claim 2, wherein said viral antigen comprises a hepatitis C viral antigen.

11. The method of claim 3, wherein said viral antigen comprises a hepatitis C viral antigen.

12. The method of claim 4, wherein said viral antigen comprises a hepatitis C viral antigen.

13. The method of claim 1, wherein said viral antigen comprises an NS3 antigen.

14. The method of claim 2, wherein said viral antigen comprises an NS3 antigen.

15. The method of claim 3, wherein said viral antigen comprises an NS3 antigen.

16. The method of claim 4, wherein said viral antigen comprises an NS3 antigen.

17. The method of claim 1, wherein said viral antigen comprises an NS4A antigen.

18. The method of claim 2, wherein said viral antigen comprises an NS4A antigen.

19. The method of claim 3, wherein said viral antigen comprises an NS4A antigen.

20. The method of claim 4, wherein said viral antigen comprises an NS4A antigen.

21. The method of claim 1, wherein said immunogenic composition is provided to said subject transdermally.

22. The method of claim 1, wherein said immunogenic composition is provided to said subject intranasally.

23. The method of claim 1, wherein said immunogenic composition comprises an oil.

24. The method of claim 1, wherein said immunogenic composition is formulated for use with an injection device.

25. The method of claim 24, wherein said injection device is an electrical injection device.

26. The method of claim 24, wherein said injection device is a needleless injection device.

27. A method of producing a T cell response to a hepatitis viral antigen in a subject in need thereof consisting essentially of providing, in a single administration, an immunogenic composition that comprises an effective amount of ribavirin and said hepatitis viral antigen to said subject.

28. The method of claim 27, further comprising identifying said subject as one in need of a T cell response to said hepatitis viral antigen.

29. The method of claim 27, further comprising measuring the T cell response to said hepatitis viral antigen.

30. The method of claim 28, further comprising measuring the T cell response to said hepatitis viral antigen.

31. The method of claim 27, wherein said hepatitis antigen is an antigen from hepatitis B virus or hepatitis C virus.

32. The method of claim 28, wherein said hepatitis antigen is an antigen from hepatitis B virus or hepatitis C virus.

33. The method of claim 29, wherein said hepatitis antigen is an antigen from hepatitis B virus or hepatitis C virus.

34. The method of claim 30, wherein said hepatitis antigen is an antigen from hepatitis B virus or hepatitis C virus.

35. The method of claim 27, wherein said viral antigen comprises a hepatitis C viral antigen.

36. The method of claim 28, wherein said viral antigen comprises a hepatitis C viral antigen.

37. The method of claim 29, wherein said viral antigen comprises a hepatitis C viral antigen.

38. The method of claim 30, wherein said viral antigen comprises a hepatitis C viral antigen.

39. The method of claim 27, wherein said viral antigen comprises an NS3 antigen.

40. The method of claim 28, wherein said viral antigen comprises an NS3 antigen.

41. The method of claim 29, wherein said viral antigen comprises an NS3 antigen.

42. The method of claim 30, wherein said viral antigen comprises an NS3 antigen.

43. The method of claim 27, wherein said viral antigen comprises an NS4A antigen.

44. The method of claim 28, wherein said viral antigen comprises an NS4A antigen.

45. The method of claim 29, wherein said viral antigen comprises an NS4A antigen.

46. The method of claim 30, wherein said viral antigen comprises an NS4A antigen.

47. The method of claim 27, wherein said immunogenic composition is provided to said subject transdermally.

48. The method of claim 27, wherein said immunogenic composition is provided to said subject intranasally.

49. The method of claim 27, wherein said immunogenic composition comprises an oil.

50. The method of claim 27, wherein said immunogenic composition is formulated for use with an injection device.

51. The method of claim 50, wherein said injection device is an electrical injection device.

52. The method of claim 50, wherein said injection device is a needleless injection device.

* * * * *

SEQUENCE LISTING

```
<160> NUMBER OF SEQ ID NOS: 15

<210> SEQ ID NO 1
<211> LENGTH: 3011
<212> TYPE: PRT
<213> ORGANISM: Artificial Sequence
<220> FEATURE:
<223> OTHER INFORMATION: Hepatitis C virus sequence

<400> SEQUENCE: 1

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45
```

```
Thr Arg Lys Thr Ser Glu Arg Ser Gln Pro Arg Gly Arg Arg Gln Pro
     50                  55                  60

Ile Pro Lys Ala Arg Arg Pro Glu Gly Arg Thr Trp Ala Gln Pro Gly
 65              70                  75                      80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Gln Val Arg Asn Ser Ser Gly Leu Tyr His Val Thr Asn Asp Cys Pro
            195                 200                 205

Asn Ser Ser Val Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
            275                 280                 285

Gln Leu Phe Thr Phe Ser Pro Arg His His Trp Thr Thr Gln Asp Cys
    290                 295                 300

Asn Cys Ser Ile Tyr Pro Gly His Ile Thr Gly His Arg Met Ala Trp
305                 310                 315                 320

Asn Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Lys Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
                420                 425                 430

Leu Asn Thr Gly Trp Leu Ala Gly Leu Phe Tyr Gln His Lys Phe Asn
            435                 440                 445

Ser Ser Gly Cys Pro Glu Arg Leu Ala Ser Cys Arg Arg Leu Thr Asp
450                 455                 460
```

-continued

```
Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Arg Pro Cys Gly Ile
                485                 490                 495

Val Pro Ala Lys Ser Val Cys Gly Pro Val Tyr Cys Phe Thr Pro Ser
                500                 505                 510

Pro Val Val Gly Thr Thr Asp Arg Ser Gly Ala Pro Thr Tyr Ser
            515                 520                 525

Trp Gly Ala Asn Asp Thr Asp Val Phe Val Leu Asn Asn Thr Arg Pro
        530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Leu Cys Pro Thr Asp Cys Phe Arg Lys Tyr Pro Glu Ala
            580                 585                 590

Thr Tyr Ser Arg Cys Gly Ser Gly Pro Arg Ile Thr Pro Arg Cys Met
        595                 600                 605

Val Asp Tyr Pro Tyr Arg Leu Trp His Tyr Pro Cys Thr Ile Asn Tyr
610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
850                 855                 860

Asn Val Arg Gly Gly Arg Asp Ala Val Ile Leu Leu Thr Cys Val Val
865                 870                 875                 880

His Pro Ala Leu Val Phe Asp Ile Thr Lys Leu Leu Leu Ala Ile Phe
```

-continued

```
                885                 890                 895
Gly Pro Leu Trp Ile Leu Gln Ala Ser Leu Leu Lys Val Pro Tyr Phe
            900                 905                 910
Val Arg Val Gln Gly Leu Leu Arg Ile Cys Ala Leu Ala Arg Lys Ile
            915                 920                 925
Ala Gly Gly His Tyr Val Gln Met Ala Ile Ile Lys Leu Gly Ala Leu
            930                 935                 940
Thr Gly Thr Cys Val Tyr Asn His Leu Ala Pro Leu Arg Asp Trp Ala
945                 950                 955                 960
His Asn Gly Leu Arg Asp Leu Ala Val Ala Val Glu Pro Val Val Phe
                965                 970                 975
Ser Arg Met Glu Thr Lys Leu Ile Thr Trp Gly Ala Asp Thr Ala Ala
            980                 985                 990
Cys Gly Asp Ile Ile Asn Gly Leu Pro Val Ser Ala Arg Arg Gly Gln
            995                 1000                1005
Glu Ile Leu Leu Gly Pro Ala Asp Gly Met Val Ser Lys Gly Trp Arg
            1010                1015                1020
Leu Leu Ala Pro Ile Thr Ala Tyr Ala Gln Gln Thr Arg Gly Leu Leu
1025                1030                1035                1040
Gly Cys Ile Ile Thr Ser Leu Thr Gly Arg Asp Lys Asn Gln Val Glu
                1045                1050                1055
Gly Glu Val Gln Ile Val Ser Thr Ala Thr Gln Thr Phe Leu Ala Thr
            1060                1065                1070
Cys Ile Asn Gly Val Cys Trp Thr Val Tyr His Gly Ala Gly Thr Arg
            1075                1080                1085
Thr Ile Ala Ser Pro Lys Gly Pro Val Ile Gln Thr Tyr Thr Asn Val
            1090                1095                1100
Asp Gln Asp Leu Val Gly Trp Pro Ala Pro Gln Gly Ser Arg Ser Leu
1105                1110                1115                1120
Thr Pro Cys Thr Cys Gly Ser Ser Asp Leu Tyr Leu Val Thr Arg His
                1125                1130                1135
Ala Asp Val Ile Pro Val Arg Arg Arg Gly Asp Ser Arg Gly Ser Leu
            1140                1145                1150
Leu Ser Pro Arg Pro Ile Ser Tyr Leu Lys Gly Ser Ser Gly Gly Pro
            1155                1160                1165
Leu Leu Cys Pro Thr Gly His Ala Val Gly Leu Phe Arg Ala Ala Val
            1170                1175                1180
Cys Thr Arg Gly Val Ala Lys Ala Val Asp Phe Ile Pro Val Glu Asn
1185                1190                1195                1200
Leu Glu Thr Thr Met Arg Ser Pro Val Phe Thr Asp Asn Ser Ser Pro
                1205                1210                1215
Pro Ala Val Pro Gln Ser Phe Gln Val Ala His Leu His Ala Pro Thr
            1220                1225                1230
Gly Ser Gly Lys Ser Thr Lys Val Pro Ala Ala Tyr Ala Ala Lys Gly
            1235                1240                1245
Tyr Lys Val Leu Val Leu Asn Pro Ser Val Ala Ala Thr Leu Gly Phe
            1250                1255                1260
Gly Ala Tyr Met Ser Lys Ala His Gly Val Asp Pro Asn Ile Arg Thr
1265                1270                1275                1280
Gly Val Arg Thr Ile Thr Thr Gly Ser Pro Ile Thr Tyr Ser Thr Tyr
                1285                1290                1295
Gly Lys Phe Leu Ala Asp Ala Gly Cys Ser Gly Gly Ala Tyr Asp Ile
            1300                1305                1310
```

```
-continued

Ile Ile Cys Asp Glu Cys His Ser Thr Asp Ala Thr Ser Ile Ser Gly
        1315                1320                1325

Ile Gly Thr Val Leu Asp Gln Ala Glu Thr Ala Gly Ala Arg Leu Val
        1330                1335                1340

Val Leu Ala Thr Ala Thr Pro Pro Gly Ser Val Thr Val Ser His Pro
1345                1350                1355                1360

Asn Ile Glu Glu Val Ala Leu Ser Thr Thr Gly Glu Ile Pro Phe Tyr
        1365                1370                1375

Gly Lys Ala Ile Pro Leu Glu Val Ile Lys Gly Gly Arg His Leu Ile
        1380                1385                1390

Phe Cys His Ser Lys Lys Lys Cys Asp Glu Leu Ala Ala Lys Leu Val
        1395                1400                1405

Ala Leu Gly Ile Asn Ala Val Ala Tyr Tyr Arg Gly Leu Asp Val Ser
        1410                1415                1420

Val Ile Pro Thr Ser Gly Asp Val Val Val Ser Thr Asp Ala Leu
1425                1430                1435                1440

Met Thr Gly Phe Thr Gly Asp Phe Asp Ser Val Ile Asp Cys Asn Thr
        1445                1450                1455

Cys Val Thr Gln Thr Val Asp Phe Ser Leu Asp Pro Thr Phe Thr Ile
        1460                1465                1470

Glu Thr Thr Thr Leu Pro Gln Asp Ala Val Ser Arg Thr Gln Arg Arg
        1475                1480                1485

Gly Arg Thr Gly Arg Gly Lys Pro Gly Ile Tyr Arg Phe Val Ala Pro
        1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
        1525                1530                1535

Val Arg Leu Arg Ala Tyr Met Asn Thr Pro Gly Leu Pro Val Cys Gln
        1540                1545                1550

Asp His Leu Gly Phe Trp Glu Gly Val Phe Thr Gly Leu Thr His Ile
        1555                1560                1565

Asp Ala His Phe Leu Ser Gln Thr Lys Gln Ser Gly Glu Asn Phe Pro
        1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Arg Lys Cys Leu Ile Arg Leu Lys Pro
        1605                1610                1615

Thr Leu His Gly Pro Thr Pro Leu Leu Tyr Arg Leu Gly Ala Val Gln
        1620                1625                1630

Asn Glu Val Thr Leu Thr His Pro Ile Thr Lys Tyr Ile Met Thr Cys
        1635                1640                1645

Met Ser Ala Asp Leu Glu Val Val Thr Ser Thr Trp Val Leu Val Gly
        1650                1655                1660

Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
        1685                1690                1695

Asp Arg Glu Val Leu Tyr Gln Glu Phe Asp Glu Met Glu Glu Cys Ser
        1700                1705                1710

Gln His Leu Pro Tyr Ile Glu Gln Gly Met Met Leu Ala Glu Gln Phe
        1715                1720                1725
```

-continued

Lys Gln Lys Ala Leu Gly Leu Leu Gln Thr Ala Ser Arg His Ala Glu
1730                1735                1740

Val Ile Thr Pro Ala Val Gln Thr Asn Trp Gln Lys Leu Glu Val Phe
1745                1750                1755                1760

Trp Ala Lys His Met Trp Asn Phe Ile Ser Gly Ile Gln Tyr Leu Ala
            1765                1770                1775

Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Gly Gln Thr Leu Leu
            1795                1800                1805

Phe Asn Ile Leu Gly Gly Trp Val Ala Ala Gln Leu Ala Ala Pro Gly
            1810                1815                1820

Ala Ala Thr Ala Phe Val Gly Ala Gly Leu Ala Gly Ala Ala Leu Asp
1825                1830                1835                1840

Ser Val Gly Leu Gly Lys Val Leu Val Asp Ile Leu Ala Gly Tyr Gly
            1845                1850                1855

Ala Gly Val Ala Gly Ala Leu Val Ala Phe Lys Ile Met Ser Gly Glu
            1860                1865                1870

Val Pro Ser Thr Glu Asp Leu Val Asn Leu Leu Pro Ala Ile Leu Ser
            1875                1880                1885

Pro Gly Ala Leu Ala Val Gly Val Val Phe Ala Ser Ile Leu Arg Arg
            1890                1895                1900

Arg Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
            1925                1930                1935

Glu Ser Asp Ala Ala Arg Val Thr Ala Ile Leu Ser Ser Leu Thr
            1940                1945                1950

Val Thr Gln Leu Leu Arg Arg Leu His Gln Trp Ile Ser Ser Glu Cys
            1955                1960                1965

Thr Thr Pro Cys Ser Gly Ser Trp Leu Arg Asp Ile Trp Asp Trp Ile
            1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
            2005                2010                2015

Gly Val Trp Arg Gly Asp Gly Ile Met His Thr Arg Cys His Cys Gly
            2020                2025                2030

Ala Glu Ile Thr Gly His Val Lys Asn Gly Thr Met Arg Ile Val Gly
            2035                2040                2045

Pro Arg Thr Cys Lys Asn Met Trp Ser Gly Thr Phe Phe Ile Asn Ala
            2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
            2085                2090                2095

Gly Asp Phe His Tyr Val Ser Gly Met Thr Thr Asp Asn Leu Lys Cys
            2100                2105                2110

Pro Cys Gln Ile Pro Ser Pro Glu Phe Phe Thr Glu Leu Asp Gly Val
            2115                2120                2125

Arg Leu His Arg Phe Ala Pro Pro Cys Lys Pro Leu Leu Arg Glu Glu
            2130                2135                2140

Val Ser Phe Arg Val Gly Leu His Glu Tyr Pro Val Gly Ser Gln Leu

-continued

```
           2145                2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
                2180                2185                2190

Gly Ser Pro Pro Ser Met Ala Ser Ser Ala Ser Gln Leu Ser Ala
                2195                2200                2205

Pro Ser Leu Lys Ala Thr Cys Thr Ala Asn His Asp Ser Pro Asp Ala
                2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
                2245                2250                2255

Asp Pro Leu Val Ala Glu Glu Asp Glu Arg Glu Val Ser Val Pro Ala
                2260                2265                2270

Glu Ile Leu Arg Lys Ser Arg Arg Phe Ala Pro Ala Leu Pro Val Trp
                2275                2280                2285

Ala Arg Pro Asp Tyr Asn Pro Leu Leu Val Glu Thr Trp Lys Lys Pro
                2290                2295                2300

Asp Tyr Glu Pro Pro Val Val His Gly Cys Pro Leu Pro Pro Arg
2305                2310                2315                2320

Ser Pro Pro Val Pro Pro Arg Lys Lys Arg Thr Val Val Leu Thr
                2325                2330                2335

Glu Ser Thr Leu Pro Thr Ala Leu Ala Glu Leu Ala Thr Lys Ser Phe
                2340                2345                2350

Gly Ser Ser Ser Thr Ser Gly Ile Thr Gly Asp Asn Thr Thr Thr Ser
                2355                2360                2365

Ser Glu Pro Ala Pro Ser Gly Cys Pro Pro Asp Ser Asp Val Glu Ser
                2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Ser Gly Ala Asp Thr Glu Asp
                2405                2410                2415

Val Val Cys Cys Ser Met Ser Tyr Ser Trp Thr Gly Ala Leu Val Thr
                2420                2425                2430

Pro Cys Ala Ala Glu Glu Gln Lys Leu Pro Ile Asn Ala Leu Ser Asn
                2435                2440                2445

Ser Leu Leu Arg His His Asn Leu Val Tyr Ser Thr Thr Ser Arg Ser
                2450                2455                2460

Ala Cys Gln Arg Lys Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
                2485                2490                2495

Lys Val Lys Ala Asn Leu Leu Ser Val Glu Glu Ala Cys Ser Leu Ala
                2500                2505                2510

Pro Pro His Ser Ala Lys Ser Lys Phe Gly Tyr Gly Ala Lys Asp Val
                2515                2520                2525

Arg Cys His Ala Arg Lys Ala Val Ala His Ile Asn Ser Val Trp Lys
                2530                2535                2540

Asp Leu Leu Glu Asp Ser Val Thr Pro Ile Asp Thr Thr Ile Met Ala
2545                2550                2555                2560

Lys Asn Glu Val Phe Cys Val Gln Pro Glu Lys Gly Gly Arg Lys Pro
                2565                2570                2575
```

```
Ala Arg Leu Ile Val Phe Pro Asp Leu Gly Val Arg Val Cys Glu Lys
            2580                2585                2590

Met Ala Leu Tyr Asp Val Val Ser Lys Leu Pro Leu Ala Val Met Gly
            2595                2600                2605

Ser Ser Tyr Gly Phe Gln Tyr Ser Pro Gly Gln Arg Val Glu Phe Leu
            2610                2615                2620

Val Gln Ala Trp Lys Ser Lys Lys Thr Pro Met Gly Leu Ser Tyr Asp
2625                2630                2635                2640

Thr Arg Cys Phe Asp Ser Thr Val Thr Glu Ser Asp Ile Arg Thr Glu
            2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
            2675                2680                2685

Ser Arg Gly Glu Asn Cys Gly Tyr Arg Arg Cys Arg Ala Ser Arg Val
            2690                2695                2700

Leu Thr Thr Ser Cys Gly Asn Thr Leu Thr Arg Tyr Ile Lys Ala Arg
2705                2710                2715                2720

Ala Ala Cys Arg Ala Ala Gly Leu Gln Asp Cys Thr Met Leu Val Cys
            2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
            2755                2760                2765

Pro Pro Gly Asp Pro Pro Gln Pro Glu Tyr Asp Leu Glu Leu Ile Thr
            2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
            2835                2840                2845

Phe Phe Ser Val Leu Ile Ala Arg Asp Gln Leu Glu Gln Ala Leu Asn
            2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
            2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Trp Ser Val Arg
            2915                2920                2925

Ala Arg Leu Leu Ala Arg Gly Gly Lys Ala Ala Ile Cys Gly Lys Tyr
            2930                2935                2940

Leu Phe Asn Trp Ala Val Arg Thr Lys Leu Lys Leu Thr Pro Ile Thr
2945                2950                2955                2960

Ala Ala Gly Arg Leu Asp Leu Ser Gly Trp Phe Thr Ala Gly Tyr Ser
            2965                2970                2975

Gly Gly Asp Ile Tyr His Ser Val Ser His Ala Arg Pro Arg Trp Phe
            2980                2985                2990
```

```
Trp Phe Cys Leu Leu Leu Leu Ala Ala Gly Val Gly Ile Tyr Leu Leu
        2995                3000                3005

Pro Asn Arg
    3010
```

<210> SEQ ID NO 2
<211> LENGTH: 182
<212> TYPE: PRT
<213> ORGANISM: Artificial Sequence
<220> FEATURE:
<223> OTHER INFORMATION: Hepatitis C virus core protein sequence

<400> SEQUENCE: 2

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu
            180
```

<210> SEQ ID NO 3
<211> LENGTH: 197
<212> TYPE: PRT
<213> ORGANISM: Artificial Sequence
<220> FEATURE:
<223> OTHER INFORMATION: Hepatitis C virus E1 protein sequence

<400> SEQUENCE: 3

```
Ser Cys Leu Thr Val Pro Ala Ser Ala Tyr Gln Val Arg Asn Ser Ser
 1               5                  10                  15

Gly Leu Tyr His Val Thr Asn Asp Cys Pro Asn Ser Ser Val Val Tyr
             20                  25                  30

Glu Ala Ala Asp Ala Ile Leu His Thr Pro Gly Cys Val Pro Cys Val
         35                  40                  45

Arg Glu Gly Asn Ala Ser Arg Cys Trp Val Ala Val Thr Pro Thr Val
     50                  55                  60

Ala Thr Arg Asp Gly Lys Leu Pro Thr Thr Gln Leu Arg Arg His Ile
 65                  70                  75                  80

Asp Leu Leu Val Gly Ser Ala Thr Leu Cys Ser Ala Leu Tyr Val Gly
                 85                  90                  95
```

```
Asp Leu Cys Gly Ser Val Phe Leu Val Gly Gln Leu Phe Thr Phe Ser
            100                 105                 110

Pro Arg His His Trp Thr Thr Gln Asp Cys Asn Cys Ser Ile Tyr Pro
            115                 120                 125

Gly His Ile Thr Gly His Arg Met Ala Trp Asn Met Met Met Asn Trp
            130                 135                 140

Ser Pro Thr Ala Ala Leu Val Val Ala Gln Leu Leu Arg Ile Pro Gln
145                 150                 155                 160

Ala Ile Met Asp Met Ile Ala Gly Ala His Trp Gly Val Leu Ala Gly
                165                 170                 175

Ile Lys Tyr Phe Ser Met Val Gly Asn Trp Ala Lys Val Leu Val Val
            180                 185                 190

Leu Leu Leu Phe Ala
            195

<210> SEQ ID NO 4
<211> LENGTH: 350
<212> TYPE: PRT
<213> ORGANISM: Artificial Sequence
<220> FEATURE:
<223> OTHER INFORMATION: Hepatitis C virus E2 protein sequence

<400> SEQUENCE: 4

Gly Val Asp Ala Glu Thr His Val Thr Gly Gly Asn Ala Gly Arg Thr
1               5                   10                  15

Thr Ala Gly Leu Val Gly Leu Leu Thr Pro Gly Ala Lys Gln Asn Ile
            20                  25                  30

Gln Leu Ile Asn Thr Asn Gly Ser Trp His Ile Asn Ser Thr Ala Leu
        35                  40                  45

Asn Cys Asn Glu Ser Leu Asn Thr Gly Trp Leu Ala Gly Leu Phe Tyr
    50                  55                  60

Gln His Lys Phe Asn Ser Ser Gly Cys Pro Glu Arg Leu Ala Ser Cys
65                  70                  75                  80

Arg Arg Leu Thr Asp Phe Ala Gln Gly Trp Gly Pro Ile Ser Tyr Ala
                85                  90                  95

Asn Gly Ser Gly Leu Asp Glu Arg Pro Tyr Cys Trp His Tyr Pro Pro
            100                 105                 110

Arg Pro Cys Gly Ile Val Pro Ala Lys Ser Val Cys Gly Pro Val Tyr
            115                 120                 125

Cys Phe Thr Pro Ser Pro Val Val Gly Thr Thr Asp Arg Ser Gly
            130                 135                 140

Ala Pro Thr Tyr Ser Trp Gly Ala Asn Asp Thr Asp Val Phe Val Leu
145                 150                 155                 160

Asn Asn Thr Arg Pro Pro Leu Gly Asn Trp Phe Gly Cys Thr Trp Met
                165                 170                 175

Asn Ser Thr Gly Phe Thr Lys Val Cys Gly Ala Pro Pro Cys Val Ile
            180                 185                 190

Gly Gly Val Gly Asn Asn Thr Leu Leu Cys Pro Thr Asp Cys Phe Arg
            195                 200                 205

Lys Tyr Pro Glu Ala Thr Tyr Ser Arg Cys Gly Ser Gly Pro Arg Ile
            210                 215                 220

Thr Pro Arg Cys Met Val Asp Tyr Pro Tyr Arg Leu Trp His Tyr Pro
225                 230                 235                 240

Cys Thr Ile Asn Tyr Thr Ile Phe Lys Val Arg Met Tyr Val Gly Gly
                245                 250                 255
```

```
Val Glu His Arg Leu Glu Ala Ala Cys Asn Trp Thr Arg Gly Glu Arg
            260                 265                 270

Cys Asp Leu Glu Asp Arg Asp Arg Ser Glu Leu Ser Pro Leu Leu Leu
            275                 280                 285

Ser Thr Thr Gln Trp Gln Val Leu Pro Cys Ser Phe Thr Thr Leu Pro
            290                 295                 300

Ala Leu Ser Thr Gly Leu Ile His Leu His Gln Asn Ile Val Asp Val
305                 310                 315                 320

Gln Tyr Leu Tyr Gly Val Gly Ser Ser Ile Ala Ser Trp Ala Ile Lys
                325                 330                 335

Trp Glu Tyr Val Val Leu Leu Phe Leu Leu Leu Ala Asp Ala
                340                 345                 350

<210> SEQ ID NO 5
<211> LENGTH: 315
<212> TYPE: PRT
<213> ORGANISM: Artificial Sequence
<220> FEATURE:
<223> OTHER INFORMATION: Hepatitis C virus NS2 protein sequence

<400> SEQUENCE: 5

Arg Val Cys Ser Cys Leu Trp Met Met Leu Leu Ile Ser Gln Ala Glu
1               5                   10                  15

Ala Ala Leu Glu Asn Leu Val Ile Leu Asn Ala Ala Ser Leu Ala Gly
            20                  25                  30

Thr His Gly Leu Val Ser Phe Leu Val Phe Phe Cys Phe Ala Trp Tyr
            35                  40                  45

Leu Lys Gly Arg Trp Val Pro Gly Ala Val Tyr Ala Leu Tyr Gly Met
    50                  55                  60

Trp Pro Leu Leu Leu Leu Leu Ala Leu Pro Gln Arg Ala Tyr Ala
65                  70                  75                  80

Leu Asp Thr Glu Val Ala Ala Ser Cys Gly Gly Val Val Leu Val Gly
                85                  90                  95

Leu Met Ala Leu Thr Leu Ser Pro Tyr Tyr Lys Arg Tyr Ile Ser Trp
            100                 105                 110

Cys Met Trp Trp Leu Gln Tyr Phe Leu Thr Arg Val Glu Ala Gln Leu
            115                 120                 125

His Val Trp Val Pro Pro Leu Asn Val Arg Gly Gly Arg Asp Ala Val
            130                 135                 140

Ile Leu Leu Thr Cys Val Val His Pro Ala Leu Val Phe Asp Ile Thr
145                 150                 155                 160

Lys Leu Leu Leu Ala Ile Phe Gly Pro Leu Trp Ile Leu Gln Ala Ser
                165                 170                 175

Leu Leu Lys Val Pro Tyr Phe Val Arg Val Gln Gly Leu Leu Arg Ile
            180                 185                 190

Cys Ala Leu Ala Arg Lys Ile Ala Gly Gly His Tyr Val Gln Met Ala
            195                 200                 205

Ile Ile Lys Leu Gly Ala Leu Thr Gly Thr Cys Val Tyr Asn His Leu
            210                 215                 220

Ala Pro Leu Arg Asp Trp Ala His Asn Gly Leu Arg Asp Leu Ala Val
225                 230                 235                 240

Ala Val Glu Pro Val Val Phe Ser Arg Met Glu Thr Lys Leu Ile Thr
                245                 250                 255

Trp Gly Ala Asp Thr Ala Ala Cys Gly Asp Ile Ile Asn Gly Leu Pro
            260                 265                 270
```

```
Val Ser Ala Arg Arg Gly Gln Glu Ile Leu Leu Gly Pro Ala Asp Gly
        275                 280                 285

Met Val Ser Lys Gly Trp Arg Leu Leu Ala Pro Ile Thr Ala Tyr Ala
        290                 295                 300

Gln Gln Thr Arg Gly Leu Leu Gly Cys Ile Ile
305                 310                 315

<210> SEQ ID NO 6
<211> LENGTH: 613
<212> TYPE: PRT
<213> ORGANISM: Artificial Sequence
<220> FEATURE:
<223> OTHER INFORMATION: Hepatitis C virus NS3 protein sequence

<400> SEQUENCE: 6

Thr Ser Leu Thr Gly Arg Asp Lys Asn Gln Val Glu Gly Glu Val Gln
  1               5                  10                  15

Ile Val Ser Thr Ala Thr Gln Thr Phe Leu Ala Thr Cys Ile Asn Gly
             20                  25                  30

Val Cys Trp Thr Val Tyr His Gly Ala Gly Thr Arg Thr Ile Ala Ser
         35                  40                  45

Pro Lys Gly Pro Val Ile Gln Thr Tyr Thr Asn Val Asp Gln Asp Leu
     50                  55                  60

Val Gly Trp Pro Ala Pro Gln Gly Ser Arg Ser Leu Thr Pro Cys Thr
 65                  70                  75                  80

Cys Gly Ser Ser Asp Leu Tyr Leu Val Thr Arg His Ala Asp Val Ile
                 85                  90                  95

Pro Val Arg Arg Arg Gly Asp Ser Arg Gly Ser Leu Leu Ser Pro Arg
            100                 105                 110

Pro Ile Ser Tyr Leu Lys Gly Ser Ser Gly Gly Pro Leu Leu Cys Pro
        115                 120                 125

Thr Gly His Ala Val Gly Leu Phe Arg Ala Ala Val Cys Thr Arg Gly
    130                 135                 140

Val Ala Lys Ala Val Asp Phe Ile Pro Val Glu Asn Leu Glu Thr Thr
145                 150                 155                 160

Met Arg Ser Pro Val Phe Thr Asp Asn Ser Ser Pro Pro Ala Val Pro
                165                 170                 175

Gln Ser Phe Gln Val Ala His Leu His Ala Pro Thr Gly Ser Gly Lys
            180                 185                 190

Ser Thr Lys Val Pro Ala Ala Tyr Ala Ala Lys Gly Tyr Lys Val Leu
        195                 200                 205

Val Leu Asn Pro Ser Val Ala Ala Thr Leu Gly Phe Gly Ala Tyr Met
    210                 215                 220

Ser Lys Ala His Gly Val Asp Pro Asn Ile Arg Thr Gly Val Arg Thr
225                 230                 235                 240

Ile Thr Thr Gly Ser Pro Ile Thr Tyr Ser Thr Tyr Gly Lys Phe Leu
                245                 250                 255

Ala Asp Ala Gly Cys Ser Gly Gly Ala Tyr Asp Ile Ile Ile Cys Asp
            260                 265                 270

Glu Cys His Ser Thr Asp Ala Thr Ser Ile Ser Gly Ile Gly Thr Val
        275                 280                 285

Leu Asp Gln Ala Glu Thr Ala Gly Ala Arg Leu Val Val Leu Ala Thr
    290                 295                 300

Ala Thr Pro Pro Gly Ser Val Thr Val Ser His Pro Asn Ile Glu Glu
305                 310                 315                 320
```

Val Ala Leu Ser Thr Thr Gly Glu Ile Pro Phe Tyr Gly Lys Ala Ile
            325                 330                 335

Pro Leu Glu Val Ile Lys Gly Arg His Leu Ile Phe Cys His Ser
            340                 345                 350

Lys Lys Lys Cys Asp Glu Leu Ala Ala Lys Leu Val Ala Leu Gly Ile
            355                 360                 365

Asn Ala Val Ala Tyr Tyr Arg Gly Leu Asp Val Ser Val Ile Pro Thr
            370                 375                 380

Ser Gly Asp Val Val Val Ser Thr Asp Ala Leu Met Thr Gly Phe
385                 390                 395                 400

Thr Gly Asp Phe Asp Ser Val Ile Asp Cys Asn Thr Cys Val Thr Gln
            405                 410                 415

Thr Val Asp Phe Ser Leu Asp Pro Thr Phe Thr Ile Glu Thr Thr Thr
            420                 425                 430

Leu Pro Gln Asp Ala Val Ser Arg Thr Gln Arg Arg Gly Arg Thr Gly
            435                 440                 445

Arg Gly Lys Pro Gly Ile Tyr Arg Phe Val Ala Pro Gly Glu Arg Pro
            450                 455                 460

Ser Gly Met Phe Asp Ser Ser Val Leu Cys Glu Cys Tyr Asp Ala Gly
465                 470                 475                 480

Cys Ala Trp Tyr Glu Leu Thr Pro Ala Glu Thr Thr Val Arg Leu Arg
            485                 490                 495

Ala Tyr Met Asn Thr Pro Gly Leu Pro Val Cys Gln Asp His Leu Gly
            500                 505                 510

Phe Trp Glu Gly Val Phe Thr Gly Leu Thr His Ile Asp Ala His Phe
            515                 520                 525

Leu Ser Gln Thr Lys Gln Ser Gly Glu Asn Phe Pro Tyr Leu Val Ala
            530                 535                 540

Tyr Gln Ala Thr Val Cys Ala Arg Ala Gln Ala Pro Pro Pro Ser Trp
545                 550                 555                 560

Asp Gln Met Arg Lys Cys Leu Ile Arg Leu Lys Pro Thr Leu His Gly
            565                 570                 575

Pro Thr Pro Leu Leu Tyr Arg Leu Gly Ala Val Gln Asn Glu Val Thr
            580                 585                 590

Leu Thr His Pro Ile Thr Lys Tyr Ile Met Thr Cys Met Ser Ala Asp
            595                 600                 605

Leu Glu Val Val Thr
            610

<210> SEQ ID NO 7
<211> LENGTH: 54
<212> TYPE: PRT
<213> ORGANISM: Artificial Sequence
<220> FEATURE:
<223> OTHER INFORMATION: Hepatitis C virus NS4A protein sequence

<400> SEQUENCE: 7

Ser Thr Trp Val Leu Val Gly Gly Val Leu Ala Ala Leu Ala Ala Tyr
1               5                   10                  15

Cys Leu Ser Thr Gly Cys Val Val Ile Val Gly Arg Ile Val Leu Ser
            20                  25                  30

Gly Lys Pro Ala Ile Ile Pro Asp Arg Glu Val Leu Tyr Gln Glu Phe
            35                  40                  45

Asp Glu Met Glu Glu Cys
        50

```
<210> SEQ ID NO 8
<211> LENGTH: 260
<212> TYPE: PRT
<213> ORGANISM: Artificial Sequence
<220> FEATURE:
<223> OTHER INFORMATION: Hepatitis C virus NS4B protein sequence

<400> SEQUENCE: 8

Ser Gln His Leu Pro Tyr Ile Glu Gln Gly Met Met Leu Ala Glu Gln
  1               5                  10                  15

Phe Lys Gln Lys Ala Leu Gly Leu Leu Gln Thr Ala Ser Arg His Ala
             20                  25                  30

Glu Val Ile Thr Pro Ala Val Gln Thr Asn Trp Gln Lys Leu Glu Val
         35                  40                  45

Phe Trp Ala Lys His Met Trp Asn Phe Ile Ser Gly Ile Gln Tyr Leu
     50                  55                  60

Ala Gly Leu Ser Thr Leu Pro Gly Asn Pro Ala Ile Ala Ser Leu Met
 65                  70                  75                  80

Ala Phe Thr Ala Ala Val Thr Ser Pro Leu Thr Thr Gly Gln Thr Leu
                 85                  90                  95

Leu Phe Asn Ile Leu Gly Gly Trp Val Ala Ala Gln Leu Ala Ala Pro
            100                 105                 110

Gly Ala Ala Thr Ala Phe Val Gly Ala Gly Leu Ala Gly Ala Ala Leu
        115                 120                 125

Asp Ser Val Gly Leu Gly Lys Val Leu Val Asp Ile Leu Ala Gly Tyr
    130                 135                 140

Gly Ala Gly Val Ala Gly Ala Leu Val Ala Phe Lys Ile Met Ser Gly
145                 150                 155                 160

Glu Val Pro Ser Thr Glu Asp Leu Val Asn Leu Leu Pro Ala Ile Leu
                165                 170                 175

Ser Pro Gly Ala Leu Ala Val Gly Val Val Phe Ala Ser Ile Leu Arg
            180                 185                 190

Arg Arg Val Gly Pro Gly Glu Gly Ala Val Gln Trp Met Asn Arg Leu
        195                 200                 205

Ile Ala Phe Ala Ser Arg Gly Asn His Val Ser Pro Thr His Tyr Val
    210                 215                 220

Pro Glu Ser Asp Ala Ala Ala Arg Val Thr Ala Ile Leu Ser Ser Leu
225                 230                 235                 240

Thr Val Thr Gln Leu Leu Arg Arg Leu His Gln Trp Ile Ser Ser Glu
                245                 250                 255

Cys Thr Thr Pro
            260

<210> SEQ ID NO 9
<211> LENGTH: 1040
<212> TYPE: PRT
<213> ORGANISM: Artificial Sequence
<220> FEATURE:
<223> OTHER INFORMATION: Hepatitis C virus NS5A/B protein sequence

<400> SEQUENCE: 9

Cys Ser Gly Ser Trp Leu Arg Asp Ile Trp Asp Trp Ile Cys Glu Val
  1               5                  10                  15

Leu Ser Asp Phe Lys Thr Trp Leu Lys Ala Lys Leu Met Pro Gln Leu
             20                  25                  30

Pro Gly Ile Pro Phe Val Ser Cys Gln Arg Gly Tyr Arg Gly Val Trp
```

-continued

```
                35                    40                    45
Arg Gly Asp Gly Ile Met His Thr Arg Cys His Cys Gly Ala Glu Ile
             50                    55                    60

Thr Gly His Val Lys Asn Gly Thr Met Arg Ile Val Gly Pro Arg Thr
 65                    70                    75                    80

Cys Lys Asn Met Trp Ser Gly Thr Phe Phe Ile Asn Ala Tyr Thr Thr
                 85                    90                    95

Gly Pro Cys Thr Pro Leu Pro Ala Pro Asn Tyr Lys Phe Ala Leu Trp
             100                   105                   110

Arg Val Ser Ala Glu Glu Tyr Val Glu Ile Arg Arg Val Gly Asp Phe
         115                   120                   125

His Tyr Val Ser Gly Met Thr Thr Asp Asn Leu Lys Cys Pro Cys Gln
     130                   135                   140

Ile Pro Ser Pro Glu Phe Phe Thr Glu Leu Asp Gly Val Arg Leu His
145                   150                   155                   160

Arg Phe Ala Pro Pro Cys Lys Pro Leu Leu Arg Glu Glu Val Ser Phe
                 165                   170                   175

Arg Val Gly Leu His Glu Tyr Pro Val Gly Ser Gln Leu Pro Cys Glu
             180                   185                   190

Pro Glu Pro Asp Val Ala Val Leu Thr Ser Met Leu Thr Asp Pro Ser
         195                   200                   205

His Ile Thr Ala Glu Ala Ala Gly Arg Arg Leu Ala Arg Gly Ser Pro
     210                   215                   220

Pro Ser Met Ala Ser Ser Ser Ala Ser Gln Leu Ser Ala Pro Ser Leu
225                   230                   235                   240

Lys Ala Thr Cys Thr Ala Asn His Asp Ser Pro Asp Ala Glu Leu Ile
                 245                   250                   255

Glu Ala Asn Leu Leu Trp Arg Gln Glu Met Gly Gly Asn Ile Thr Arg
             260                   265                   270

Val Glu Ser Glu Asn Lys Val Val Ile Leu Asp Ser Phe Asp Pro Leu
         275                   280                   285

Val Ala Glu Glu Asp Glu Arg Glu Val Ser Val Pro Ala Glu Ile Leu
     290                   295                   300

Arg Lys Ser Arg Arg Phe Ala Pro Ala Leu Pro Val Trp Ala Arg Pro
305                   310                   315                   320

Asp Tyr Asn Pro Leu Leu Val Glu Thr Trp Lys Lys Pro Asp Tyr Glu
                 325                   330                   335

Pro Pro Val Val His Gly Cys Pro Leu Pro Pro Arg Ser Pro Pro
             340                   345                   350

Val Pro Pro Pro Arg Lys Lys Arg Thr Val Val Leu Thr Glu Ser Thr
         355                   360                   365

Leu Pro Thr Ala Leu Ala Glu Leu Ala Thr Lys Ser Phe Gly Ser Ser
     370                   375                   380

Ser Thr Ser Gly Ile Thr Gly Asp Asn Thr Thr Ser Ser Glu Pro
385                   390                   395                   400

Ala Pro Ser Gly Cys Pro Pro Asp Ser Asp Val Glu Ser Tyr Ser Ser
                 405                   410                   415

Met Pro Pro Leu Glu Gly Glu Pro Gly Asp Pro Asp Leu Ser Asp Gly
             420                   425                   430

Ser Trp Ser Thr Val Ser Ser Gly Ala Asp Thr Glu Asp Val Val Cys
         435                   440                   445

Cys Ser Met Ser Tyr Ser Trp Thr Gly Ala Leu Val Thr Pro Cys Ala
     450                   455                   460
```

-continued

```
Ala Glu Glu Gln Lys Leu Pro Ile Asn Ala Leu Ser Asn Ser Leu Leu
465                 470                 475                 480

Arg His His Asn Leu Val Tyr Ser Thr Thr Ser Arg Ser Ala Cys Gln
                485                 490                 495

Arg Lys Lys Lys Val Thr Phe Asp Arg Leu Gln Val Leu Asp Ser His
            500                 505                 510

Tyr Gln Asp Val Leu Lys Glu Val Lys Ala Ala Ser Lys Val Lys
            515                 520                 525

Ala Asn Leu Leu Ser Val Glu Glu Ala Cys Ser Leu Ala Pro Pro His
530                 535                 540

Ser Ala Lys Ser Lys Phe Gly Tyr Gly Ala Lys Asp Val Arg Cys His
545                 550                 555                 560

Ala Arg Lys Ala Val Ala His Ile Asn Ser Val Trp Lys Asp Leu Leu
                565                 570                 575

Glu Asp Ser Val Thr Pro Ile Asp Thr Thr Ile Met Ala Lys Asn Glu
                580                 585                 590

Val Phe Cys Val Gln Pro Glu Lys Gly Gly Arg Lys Pro Ala Arg Leu
            595                 600                 605

Ile Val Phe Pro Asp Leu Gly Val Arg Val Cys Glu Lys Met Ala Leu
610                 615                 620

Tyr Asp Val Val Ser Lys Leu Pro Leu Ala Val Met Gly Ser Ser Tyr
625                 630                 635                 640

Gly Phe Gln Tyr Ser Pro Gly Gln Arg Val Glu Phe Leu Val Gln Ala
                645                 650                 655

Trp Lys Ser Lys Lys Thr Pro Met Gly Leu Ser Tyr Asp Thr Arg Cys
                660                 665                 670

Phe Asp Ser Thr Val Thr Glu Ser Asp Ile Arg Thr Glu Glu Ala Ile
            675                 680                 685

Tyr Gln Cys Cys Asp Leu Asp Pro Gln Ala Arg Val Ala Ile Lys Ser
690                 695                 700

Leu Thr Glu Arg Leu Tyr Val Gly Gly Pro Leu Thr Asn Ser Arg Gly
705                 710                 715                 720

Glu Asn Cys Gly Tyr Arg Arg Cys Arg Ala Ser Arg Val Leu Thr Thr
                725                 730                 735

Ser Cys Gly Asn Thr Leu Thr Arg Tyr Ile Lys Ala Arg Ala Ala Cys
            740                 745                 750

Arg Ala Ala Gly Leu Gln Asp Cys Thr Met Leu Val Cys Gly Asp Asp
            755                 760                 765

Leu Val Val Ile Cys Glu Ser Ala Gly Val Gln Glu Asp Ala Ala Ser
770                 775                 780

Leu Arg Ala Phe Thr Glu Ala Met Thr Arg Tyr Ser Ala Pro Pro Gly
785                 790                 795                 800

Asp Pro Pro Gln Pro Glu Tyr Asp Leu Glu Leu Ile Thr Ser Cys Ser
                805                 810                 815

Ser Asn Val Ser Val Ala His Asp Gly Ala Gly Lys Arg Val Tyr Tyr
            820                 825                 830

Leu Thr Arg Asp Pro Thr Thr Pro Leu Ala Arg Ala Ala Trp Glu Thr
            835                 840                 845

Ala Arg His Thr Pro Val Asn Ser Trp Leu Gly Asn Ile Ile Met Phe
850                 855                 860

Ala Pro Thr Leu Trp Ala Arg Met Ile Leu Met Thr His Phe Phe Ser
865                 870                 875                 880
```

```
Val Leu Ile Ala Arg Asp Gln Leu Glu Gln Ala Leu Asn Cys Glu Ile
                885                 890                 895

Tyr Gly Ala Cys Tyr Ser Ile Glu Pro Leu Asp Leu Pro Pro Ile Ile
            900                 905                 910

Gln Arg Leu His Gly Leu Ser Ala Phe Ser Leu His Ser Tyr Ser Pro
        915                 920                 925

Gly Glu Ile Asn Arg Val Ala Ala Cys Leu Arg Lys Leu Gly Val Pro
    930                 935                 940

Pro Leu Arg Ala Trp Arg His Arg Ala Trp Ser Val Arg Ala Arg Leu
945                 950                 955                 960

Leu Ala Arg Gly Gly Lys Ala Ala Ile Cys Gly Lys Tyr Leu Phe Asn
                965                 970                 975

Trp Ala Val Arg Thr Lys Leu Lys Leu Thr Pro Ile Thr Ala Ala Gly
            980                 985                 990

Arg Leu Asp Leu Ser Gly Trp Phe Thr Ala Gly Tyr Ser Gly Gly Asp
        995                 1000                1005

Ile Tyr His Ser Val Ser His Ala Arg Pro Arg Trp Phe Trp Phe Cys
    1010                1015                1020

Leu Leu Leu Leu Ala Ala Gly Val Gly Ile Tyr Leu Leu Pro Asn Arg
1025                1030                1035                1040

<210> SEQ ID NO 10
<211> LENGTH: 226
<212> TYPE: PRT
<213> ORGANISM: Artificial Sequence
<220> FEATURE:
<223> OTHER INFORMATION: Hepatitis B virus S antigen (HBsAg) sequence

<400> SEQUENCE: 10

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Met Thr Thr Ala
        115                 120                 125

Gln Gly Thr Ser Met Tyr Pro Ser Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205
```

-continued

```
Leu Ser Pro Phe Leu Pro Leu Pro Ile Phe Phe Cys Leu Trp Val
    210                 215                 220

Tyr Ile
225

<210> SEQ ID NO 11
<211> LENGTH: 212
<212> TYPE: PRT
<213> ORGANISM: Artificial Sequence
<220> FEATURE:
<223> OTHER INFORMATION: Hepatitis B virus C antigen and e antigen
      (HBcAg/HBeAg) sequence

<400> SEQUENCE: 11

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 12
<211> LENGTH: 2227
<212> TYPE: PRT
<213> ORGANISM: Artificial Sequence
<220> FEATURE:
<223> OTHER INFORMATION: Hepatitis A virus sequence

<400> SEQUENCE: 12

Met Asn Met Ser Lys Gln Gly Ile Phe Gln Thr Val Gly Ser Gly Leu
1               5                   10                  15

Asp His Ile Leu Ser Leu Ala Asp Ile Glu Glu Glu Gln Met Ile Gln
            20                  25                  30

Ser Val Asp Arg Thr Ala Val Thr Gly Ala Ser Tyr Phe Thr Ser Val
        35                  40                  45

Asp Gln Ser Ser Val His Thr Ala Glu Val Gly Ser His Gln Ile Glu
```

-continued

```
             50                  55                  60
Pro Leu Lys Thr Ser Val Asp Lys Pro Gly Ser Lys Lys Thr Gln Gly
65                  70                  75                  80

Glu Lys Phe Phe Leu Ile His Ser Ala Asp Trp Leu Thr Thr His Ala
                85                  90                  95

Leu Phe His Glu Val Ala Lys Leu Asp Val Val Lys Leu Leu Tyr Asn
            100                 105                 110

Glu Gln Phe Ala Val Gln Gly Leu Leu Arg Tyr His Thr Tyr Ala Arg
        115                 120                 125

Phe Gly Ile Glu Ile Gln Val Gln Ile Asn Pro Thr Pro Phe Gln Gln
    130                 135                 140

Gly Gly Leu Ile Cys Ala Met Val Pro Gly Asp Gln Ser Tyr Gly Ser
145                 150                 155                 160

Ile Ala Ser Leu Thr Val Tyr Pro His Gly Leu Leu Asn Cys Asn Ile
                165                 170                 175

Asn Asn Val Val Arg Ile Lys Val Pro Phe Ile Tyr Thr Arg Gly Ala
            180                 185                 190

Tyr His Phe Lys Asp Pro Gln Tyr Pro Val Trp Glu Leu Thr Ile Arg
        195                 200                 205

Val Trp Ser Glu Leu Asn Ile Gly Thr Gly Thr Ser Ala Tyr Thr Ser
    210                 215                 220

Leu Asn Val Leu Ala Arg Phe Thr Asp Leu Glu Leu His Gly Leu Thr
225                 230                 235                 240

Pro Leu Ser Thr Gln Met Met Arg Asn Glu Phe Arg Val Ser Thr Thr
                245                 250                 255

Glu Asn Val Val Asn Leu Ser Asn Tyr Glu Asp Ala Arg Ala Lys Met
            260                 265                 270

Ser Phe Ala Leu Asp Gln Glu Asp Trp Lys Ser Asp Pro Ser Gln Gly
        275                 280                 285

Gly Gly Ile Lys Ile Thr His Phe Thr Thr Trp Thr Ser Ile Pro Thr
    290                 295                 300

Leu Ala Ala Gln Phe Pro Phe Asn Ala Ser Asp Ser Val Gly Gln Gln
305                 310                 315                 320

Ile Lys Val Ile Pro Val Asp Pro Tyr Phe Phe Gln Met Thr Asn Thr
                325                 330                 335

Asn Pro Asp Gln Lys Cys Ile Thr Ala Leu Ala Ser Ile Cys Gln Met
            340                 345                 350

Phe Cys Phe Trp Arg Gly Asp Leu Val Phe Asp Phe Gln Val Phe Pro
        355                 360                 365

Thr Lys Tyr His Ser Gly Arg Leu Leu Phe Cys Phe Val Pro Gly Asn
    370                 375                 380

Glu Leu Ile Asp Val Thr Gly Ile Thr Leu Lys Gln Ala Thr Thr Ala
385                 390                 395                 400

Pro Cys Ala Val Met Asp Ile Thr Gly Val Gln Ser Thr Leu Arg Phe
                405                 410                 415

Arg Val Pro Trp Ile Ser Asp Thr Pro Tyr Arg Val Asn Arg Tyr Thr
            420                 425                 430

Lys Ser Ala His Gln Lys Gly Glu Tyr Thr Ala Ile Gly Lys Leu Ile
        435                 440                 445

Val Tyr Cys Tyr Asn Arg Leu Thr Ser Pro Ser Asn Val Ala Ser His
    450                 455                 460

Val Arg Val Asn Val Tyr Leu Ser Ala Ile Asn Leu Glu Cys Phe Ala
465                 470                 475                 480
```

-continued

```
Pro Leu Tyr His Ala Met Asp Val Thr Thr Gln Val Gly Asp Asp Ser
            485                 490                 495
Gly Gly Phe Ser Thr Thr Val Ser Thr Glu Gln Asn Val Pro Asp Pro
        500                 505                 510
Gln Val Gly Ile Thr Thr Met Arg Asp Leu Lys Gly Lys Ala Asn Arg
        515                 520                 525
Gly Lys Met Asp Val Ser Gly Val Gln Ala Pro Arg Gly Ser Tyr Gln
    530                 535                 540
Gln Gln Leu Asn Asp Pro Val Leu Ala Lys Lys Val Pro Glu Thr Phe
545                 550                 555                 560
Pro Glu Leu Lys Pro Gly Glu Ser Arg His Thr Ser Asp His Met Ser
            565                 570                 575
Ile Tyr Lys Phe Met Gly Arg Ser His Phe Leu Cys Thr Phe Thr Phe
            580                 585                 590
Asn Ser Asn Asn Lys Glu Tyr Thr Phe Pro Ile Thr Leu Ser Ser Thr
        595                 600                 605
Ser Asn Pro Pro His Gly Leu Pro Ser Thr Leu Arg Trp Phe Phe Asn
    610                 615                 620
Leu Phe Gln Leu Tyr Arg Gly Pro Leu Asp Leu Thr Ile Ile Thr
625                 630                 635                 640
Gly Ala Thr Asp Val Asp Gly Met Ala Trp Phe Thr Pro Val Gly Leu
            645                 650                 655
Ala Val Asp Pro Trp Val Glu Lys Glu Ser Ala Leu Ser Ile Asp Tyr
            660                 665                 670
Lys Thr Ala Leu Gly Ala Val Arg Phe Asn Thr Arg Arg Thr Gly Asn
        675                 680                 685
Ile Gln Ile Arg Leu Pro Trp Tyr Ser Tyr Leu Tyr Ala Val Ser Gly
        690                 695                 700
Ala Leu Asp Gly Leu Gly Asp Lys Thr Asp Ser Thr Phe Gly Leu Phe
705                 710                 715                 720
Leu Phe Glu Ile Ala Asn Tyr Asn His Ser Asp Glu Tyr Leu Ser Phe
            725                 730                 735
Ser Cys Tyr Leu Ser Val Thr Glu Gln Ser Glu Phe Tyr Phe Pro Arg
            740                 745                 750
Ala Pro Leu Asn Ser Asn Ala Met Leu Ser Thr Glu Ser Met Met Ser
        755                 760                 765
Arg Ile Ala Ala Gly Asp Leu Glu Ser Ser Val Asp Asp Pro Arg Ser
    770                 775                 780
Glu Glu Asp Arg Arg Phe Glu Ser His Ile Glu Cys Arg Lys Pro Tyr
785                 790                 795                 800
Lys Glu Leu Arg Leu Glu Val Gly Lys Gln Arg Leu Lys Tyr Ala Gln
            805                 810                 815
Glu Glu Leu Ser Asn Glu Val Leu Pro Pro Arg Lys Met Lys Gly
            820                 825                 830
Leu Phe Ser Gln Ala Lys Ile Ser Leu Phe Tyr Thr Glu Glu His Glu
        835                 840                 845
Ile Met Lys Phe Ser Trp Arg Gly Val Thr Ala Asp Thr Arg Ala Leu
    850                 855                 860
Arg Arg Phe Gly Phe Ser Leu Ala Ala Gly Arg Ser Val Trp Thr Leu
865                 870                 875                 880
Glu Met Asp Ala Gly Val Leu Thr Gly Arg Leu Ile Arg Leu Asn Asp
            885                 890                 895
```

-continued

Glu Lys Trp Thr Glu Met Lys Asp Asp Lys Ile Val Ser Leu Ile Glu
            900                 905                 910

Lys Phe Thr Ser Asn Lys Tyr Trp Ser Lys Val Asn Phe Pro His Gly
            915                 920                 925

Met Leu Asp Leu Glu Glu Ile Ala Ala Asn Ser Lys Asp Phe Pro Asn
            930                 935                 940

Met Ser Glu Thr Asp Leu Cys Phe Leu Leu His Trp Leu Asn Pro Lys
945                 950                 955                 960

Lys Ile Asn Leu Ala Asp Arg Met Leu Gly Leu Ser Gly Val Gln Glu
            965                 970                 975

Ile Lys Glu Gln Gly Val Gly Leu Ile Ala Glu Cys Arg Thr Phe Leu
            980                 985                 990

Asp Ser Ile Ala Gly Thr Leu Lys Ser Met Met Phe Gly Phe His His
            995                1000                1005

Ser Val Thr Val Glu Ile Ile Asn Thr Val Leu Cys Phe Val Lys Ser
           1010                1015                1020

Gly Ile Leu Leu Tyr Val Ile Gln Gln Leu Asn Gln Asp Glu His Ser
1025                1030                1035                1040

His Ile Ile Gly Leu Leu Arg Val Met Asn Tyr Ala Asp Ile Gly Cys
            1045                1050                1055

Ser Val Ile Ser Cys Gly Lys Val Phe Ser Lys Met Leu Glu Thr Val
            1060                1065                1070

Phe Asn Trp Gln Met Asp Ser Arg Met Met Glu Leu Arg Thr Gln Ser
            1075                1080                1085

Phe Ser Asn Trp Leu Arg Asp Ile Cys Ser Gly Ile Thr Ile Phe Lys
            1090                1095                1100

Ser Phe Lys Asp Ala Ile Tyr Trp Leu Tyr Thr Lys Leu Lys Asp Phe
1105                1110                1115                1120

Tyr Glu Val Asn Tyr Gly Lys Lys Asp Ile Leu Asn Ile Leu Lys
            1125                1130                1135

Asp Asn Gln Gln Lys Ile Glu Lys Ala Ile Glu Glu Ala Asp Asn Phe
            1140                1145                1150

Cys Ile Leu Gln Ile Gln Asp Val Glu Lys Phe Asp Gln Tyr Gln Lys
            1155                1160                1165

Gly Val Asp Leu Ile Gln Lys Leu Arg Thr Val His Ser Met Ala Gln
            1170                1175                1180

Val Asp Pro Asn Leu Gly Val His Leu Ser Pro Leu Arg Asp Cys Ile
1185                1190                1195                1200

Ala Arg Val His Gln Lys Leu Lys Asn Leu Gly Ser Ile Asn Gln Ala
            1205                1210                1215

Met Val Thr Arg Cys Glu Pro Val Cys Tyr Leu Tyr Gly Lys Arg
            1220                1225                1230

Gly Gly Gly Lys Ser Leu Thr Ser Ile Ala Leu Ala Thr Lys Ile Cys
            1235                1240                1245

Lys His Tyr Gly Val Glu Pro Glu Lys Asn Ile Tyr Thr Lys Pro Val
            1250                1255                1260

Ala Ser Asp Tyr Trp Asp Gly Tyr Ser Gly Gln Leu Val Cys Ile Ile
1265                1270                1275                1280

Asp Asp Ile Gly Gln Asn Thr Thr Asp Glu Asp Trp Ser Asp Phe Cys
            1285                1290                1295

Gln Leu Val Ser Gly Cys Pro Met Arg Leu Asn Met Ala Ser Leu Glu
            1300                1305                1310

Glu Lys Gly Arg His Phe Ser Ser Pro Phe Ile Ile Ala Thr Ser Asn

-continued

```
            1315                1320                1325
Trp Ser Asn Pro Ser Pro Lys Thr Val Tyr Val Lys Glu Ala Ile Asp
        1330                1335                1340
Arg Arg Leu His Phe Lys Val Glu Val Lys Pro Ala Ser Phe Phe Lys
1345                1350                1355                1360
Asn Pro His Asn Asp Met Leu Asn Val Asn Leu Ala Lys Thr Asn Asp
            1365                1370                1375
Ala Ile Lys Asp Met Ser Cys Val Asp Leu Ile Met Asp Gly His Asn
        1380                1385                1390
Ile Ser Leu Met Asp Leu Leu Ser Ser Leu Val Met Thr Val Glu Ile
        1395                1400                1405
Arg Lys Gln Asn Met Ser Glu Phe Met Glu Leu Trp Ser Gln Gly Ile
        1410                1415                1420
Ser Asp Asp Asp Asn Asp Ser Ala Val Ala Glu Phe Phe Gln Ser Phe
1425                1430                1435                1440
Pro Ser Gly Glu Pro Ser Asn Trp Lys Leu Ser Ser Phe Phe Gln Ser
            1445                1450                1455
Val Thr Asn His Lys Trp Val Ala Val Gly Ala Ala Val Gly Ile Leu
        1460                1465                1470
Gly Val Leu Val Gly Gly Trp Phe Val Tyr Lys His Phe Ser Arg Lys
        1475                1480                1485
Glu Glu Glu Pro Ile Pro Ala Glu Gly Val Tyr His Gly Val Thr Lys
        1490                1495                1500
Pro Lys Gln Val Ile Lys Leu Asp Ala Asp Pro Val Glu Ser Gln Ser
1505                1510                1515                1520
Thr Leu Glu Ile Ala Gly Leu Val Arg Lys Asn Leu Val Gln Phe Gly
            1525                1530                1535
Val Gly Glu Lys Asn Gly Cys Val Arg Trp Val Met Asn Ala Leu Gly
        1540                1545                1550
Val Lys Asp Asp Trp Leu Leu Val Pro Ser His Ala Tyr Lys Phe Glu
        1555                1560                1565
Lys Asp Tyr Glu Met Met Glu Phe Tyr Phe Asn Arg Gly Gly Thr Tyr
        1570                1575                1580
Tyr Ser Ile Ser Ala Gly Asn Val Val Ile Gln Ser Leu Asp Val Gly
1585                1590                1595                1600
Phe Gln Asp Val Val Leu Met Lys Val Pro Thr Ile Pro Lys Phe Arg
            1605                1610                1615
Asp Ile Thr Gln His Phe Ile Lys Lys Gly Asp Val Pro Arg Ala Leu
        1620                1625                1630
Asn Arg Leu Ala Thr Leu Val Thr Thr Val Asn Gly Thr Pro Met Leu
        1635                1640                1645
Ile Ser Glu Gly Pro Leu Lys Met Glu Glu Lys Ala Thr Tyr Val His
        1650                1655                1660
Lys Lys Asn Asp Gly Thr Thr Val Asp Leu Thr Val Asp Gln Ala Trp
1665                1670                1675                1680
Arg Gly Lys Gly Glu Gly Leu Pro Gly Met Cys Gly Gly Ala Leu Val
            1685                1690                1695
Ser Ser Asn Gln Ser Ile Gln Asn Ala Ile Leu Gly Ile His Val Ala
        1700                1705                1710
Gly Gly Asn Ser Ile Leu Val Ala Lys Leu Val Thr Gln Glu Met Phe
        1715                1720                1725
Gln Asn Ile Asp Lys Lys Ile Glu Ser Gln Arg Ile Met Lys Val Glu
        1730                1735                1740
```

-continued

```
Phe Thr Gln Cys Ser Met Asn Val Val Ser Lys Thr Leu Phe Arg Lys
1745                1750                1755                1760

Ser Pro Ile His His His Ile Asp Lys Thr Met Ile Asn Phe Pro Ala
                1765                1770                1775

Ala Met Pro Phe Ser Lys Ala Glu Ile Asp Pro Met Ala Met Met Leu
            1780                1785                1790

Ser Lys Tyr Ser Leu Pro Ile Val Glu Pro Glu Asp Tyr Lys Glu
        1795                1800                1805

Ala Ser Val Phe Tyr Gln Asn Lys Ile Val Gly Lys Thr Gln Leu Val
    1810                1815                1820

Asp Asp Phe Leu Asp Leu Asp Met Ala Ile Thr Gly Ala Pro Gly Ile
1825                1830                1835                1840

Asp Ala Ile Asn Met Asp Ser Ser Pro Gly Phe Pro Tyr Val Gln Glu
                1845                1850                1855

Lys Leu Thr Lys Arg Asp Leu Ile Trp Leu Asp Glu Asn Gly Leu Leu
            1860                1865                1870

Leu Gly Val His Pro Arg Leu Ala Gln Arg Ile Leu Phe Asn Thr Val
        1875                1880                1885

Met Met Glu Asn Cys Ser Asp Leu Asp Val Val Phe Thr Thr Cys Pro
    1890                1895                1900

Lys Asp Glu Leu Arg Pro Leu Glu Lys Val Leu Glu Ser Lys Thr Arg
1905                1910                1915                1920

Ala Ile Asp Ala Cys Pro Leu Asp Tyr Thr Ile Leu Cys Arg Met Tyr
                1925                1930                1935

Trp Gly Pro Ala Ile Ser Tyr Phe His Leu Asn Pro Gly Phe His Thr
            1940                1945                1950

Gly Val Ala Ile Gly Ile Asp Pro Asp Arg Gln Trp Asp Glu Leu Phe
        1955                1960                1965

Lys Thr Met Ile Arg Phe Gly Asp Val Gly Leu Asp Leu Asp Phe Ser
    1970                1975                1980

Ala Phe Asp Ala Ser Leu Ser Pro Phe Met Ile Arg Glu Ala Gly Arg
1985                1990                1995                2000

Ile Met Ser Glu Leu Ser Gly Thr Pro Ser His Phe Gly Thr Ala Leu
                2005                2010                2015

Ile Asn Thr Ile Ile Tyr Ser Lys His Leu Leu Tyr Asn Cys Cys Tyr
            2020                2025                2030

His Val Cys Gly Ser Met Pro Ser Gly Ser Pro Cys Thr Ala Leu Leu
        2035                2040                2045

Asn Ser Ile Ile Asn Asn Ile Asn Leu Tyr Tyr Val Phe Ser Lys Ile
    2050                2055                2060

Phe Gly Lys Ser Pro Val Phe Phe Cys Gln Ala Leu Arg Ile Leu Cys
2065                2070                2075                2080

Tyr Gly Asp Asp Val Leu Ile Val Phe Ser Arg Asp Val Gln Ile Asp
                2085                2090                2095

Asn Leu Asp Leu Ile Gly Gln Lys Ile Val Asp Glu Phe Lys Lys Leu
            2100                2105                2110

Gly Met Thr Ala Thr Ser Ala Asp Lys Asn Val Pro Gln Leu Lys Pro
        2115                2120                2125

Val Ser Glu Leu Thr Phe Leu Lys Arg Ser Phe Asn Leu Val Glu Asp
    2130                2135                2140

Arg Ile Arg Pro Ala Ile Ser Glu Lys Thr Ile Trp Ser Leu Met Ala
2145                2150                2155                2160
```

-continued

```
Trp Gln Arg Ser Asn Ala Glu Phe Glu Gln Asn Leu Glu Asn Ala Gln
            2165                2170                2175

Trp Phe Ala Phe Met His Gly Tyr Glu Phe Tyr Gln Lys Phe Tyr Tyr
        2180                2185                2190

Phe Val Gln Ser Cys Leu Glu Lys Glu Met Ile Glu Tyr Arg Leu Lys
    2195                2200                2205

Ser Tyr Asp Trp Trp Arg Met Arg Phe Tyr Asp Gln Cys Phe Ile Cys
    2210                2215                2220

Asp Leu Ser
2225

<210> SEQ ID NO 13
<211> LENGTH: 9416
<212> TYPE: DNA
<213> ORGANISM: Artificial Sequence
<220> FEATURE:
<223> OTHER INFORMATION: Hepatitis C virus sequence

<400> SEQUENCE: 13
gccagccccc tgatggggc gacactccac catgaatcac tccctgtga ggaactactg      60 tcttcacgca gaaagcgtct agccatggcg ttagtatgag tgtcgtgcag cctccaggac    120 ccccctccc gggagagcca tagtggtctg cggaaccggt gagtacaccg gaattgccag    180
gacgaccggg tcctttcttg gataaaccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta accgtgcac catgagcacg aatcctaaac    360
ctcaaagaaa aaccaaacgt aacaccaacc gtcgcccaca ggacgtcaag ttccgggtg    420 gcggtcagat cgttggtgga gtttacttgt tgccgcgcag gggccctaga ttgggtgtgc    480
gcgcgacgag gaagacttcc gagcggtcgc aacctcgagg tagacgtcag cctatcccca    540
aggcacgtcg gcccgagggc aggacctggg ctcagcccgg gtaccttggg ccctctatg    600 gcaatgaggg ttgcgggtgg gcgggatggc tcctgtctcc ccgtggctct cggcctagct    660
ggggccccac agacccccgg cgtaggtcgc gcaatttggg taaggtcatc gataccctta    720
cgtgcggctt cgccgaccct atgggtgtaca taccgctcgt cggcgcccct cttggaggcg    780
ctgccagggc cctggcgcat gcgtccgggg ttctggaaga cggcgtgaac tatgcaacag    840
ggaaccttcc tggttgctct ttctctatct tccttctggc cctgctctct tgcctgactg    900
tgcccgcttc agcctaccaa gtgcgcaatt cctcggggct ttaccatgtc accaatgatt    960
gccctaactc gagtgttgtg tacgaggcgg ccgatgccat cctgcacact ccggggtgtg   1020
tcccttgcgt tcgcgagggt aacgcctcga ggtgttgggt ggcggtgacc ccacgggtgg   1080
ccaccaggga cggcaaactc cccacaacgc agcttcgacg tcatatcgat ctgcttgtcg   1140
ggagcgccac cctctgctcg gccctctacg tggggggacct gtgcgggtct gtctttcttg   1200
ttggtcaact gtttaccttc tctcccaggc accactggac gacgcaagac tgcaattgtt   1260
ctatctatcc cggccatata acgggtcatc gcatggcatg gaatatgatg atgaactggt   1320
cccctacggc agcgttggtg gtagctcagc tgctccgaat cccacaagcc atcatggaca   1380
tgatcgctgg cgcccactgg ggagtcctgg cgggcataaa gtatttctcc atggtgggga   1440
actgggcgaa ggtcctggta gtgctgctgc tatttgccgg cgtcgacgcg gaaacccacg   1500
tcaccggggg aaatgccggc cgcaccacgg ctgggcttgt tggtctcctt acaccaggcg   1560
ccaagcagaa catccaactg atcaacacca acggcagttg gcacatcaat agcacggcct   1620
```

```
tgaactgcaa tgaaagcctt aacaccggct ggttagcagg gctcttctat cagcacaaat   1680
tcaactcttc aggctgtcct gagaggttgg ccagctgccg acgccttacc gattttgccc   1740
agggctgggg tcctatcagt tatgccaacg aagcggcct cgacgaacgc ccctactgct    1800
ggcactaccc tccaagacct tgtggcattg tgcccgcaaa gagcgtgtgt ggcccggtat   1860
attgcttcac tcccagcccc gtggtggtgg aacgaccga caggtcgggc gcgcctacct   1920
acagctgggg tgcaaatgat acggatgtct tcgtccttaa caacaccagg ccaccgctgg   1980
gcaattggtt cggttgtacc tggatgaact caactggatt caccaaagtg tgcggagcgc   2040
ccccttgtgt catcggaggg gtgggcaaca acaccttgct ctgccccact gattgcttcc   2100
gcaaatatcc ggaagccaca tactctcggt gcggctccgg tcccaggatt acacccaggt   2160
gcatggtcga ctaccgtat aggctttggc actatccttg taccatcaat tacaccatat    2220
tcaaagtcag gatgtacgtg ggaggggtcg agcacaggct ggaagcggcc tgcaactgga   2280
cgcggggcga acgctgtgat ctggaagaca gggacaggtc cgagctcagc ccgttgctgc   2340
tgtccaccac acagtggcag gtccttccgt gttctttcac gaccctgcca gccttgtcca   2400
ccggcctcat ccacctccac cagaacattg tggacgtgca gtacttgtac ggggtagggt   2460
caagcatcgc gtcctgggcc attaagtggg agtacgtcgt tctcctgttc cttctgcttg   2520
cagacgcgcg cgtctgttcc tgcttgtgga tgatgttact catatcccaa gcggaggcgg   2580
ctttggagaa cctcgtaata ctcaatgcag catccctggc cgggacgcat ggtcttgtgt   2640
ccttcctcgt gttcttctgc tttgcgtggt atctgaaggg taggtgggtg cccggagcgg   2700
tctacgccct ctacgggatg tggcctctcc tcctgctcct gctggcgttg cctcagcggg   2760
catacgcact ggacacggag gtggccgcgt cgtgtggcgg cgttgttctt gtcgggttaa   2820
tggcgctgac tctgtcgcca tattacaagc gctatatcag ctggtgcatg tggtggcttc   2880
agtattttct gaccagagta gaagcgcaac tgcacgtgtg ggttccccccc ctcaacgtcc   2940 ggggggggcg cgatgccgtc atcttactca cgtgtgtagt acacccggcc ctggtatttg   3000
acatcaccaa actactcctg gccatcttcg gacccctttg gattcttcaa gccagtttgc   3060
ttaaagtccc ctacttcgtg cgcgttcaag gccttctccg gatctgcgcg ctagcgcgga   3120
agatagccgg aggtcattac gtgcaaatgg ccatcatcaa gttagggggcg cttactggca   3180 cctgtgtgta taaccatctc gctcctcttc gagactgggc gcacaacggc ctgcgagatc   3240
tggccgtggc tgtggaacca gtcgtcttct cccgaatgga gaccaagctc atcacgtggg   3300
gggcagatac cgccgcgtgc ggtgacatca tcaacggctt gccgcgtctct gcccgtaggg   3360 gccaggagat actgcttggg ccagccgacg gaatggtctc caaggggtgg aggttgctgg   3420
cgcccatcac ggcgtacgcc cagcagacga gaggcctcct agggtgtata atcaccagcc   3480
tgactggccg ggacaaaaac caagtggagg gtgaggtcca gatcgtgtca actgctaccc   3540
agaccttcct ggcaacgtgc atcaatgggg tatgctggac tgtctaccac ggggccggaa   3600
cgaggaccat cgcatcaccc aagggtcctg tcatccagac gtataccaat gtggatcaag   3660
acctcgtggg ctggccgct cctcaaggtt cccgctcatt gacaccctgc acctgcggct    3720
cctcggacct ttacctggtc acgaggcacg ccgatgtcat tcccgtgcgc cggcgaggtg   3780
atagcagggg tagcctgctt tcgcccggc ccatttccta cttgaaaggc tcctcggggg    3840
gtccgctgtt gtgccccacg ggacacgccg tgggcctatt cagggccgcg gtgtgcaccc   3900
gtggagtggc taaggcggtg gactttatcc ctgtggagaa cctagagaca accatgagat   3960
ccccggtgtt cacggacaac tcctctccac cagcagtgcc ccagagcttc caggtggccc   4020
```

-continued

```
acctgcatgc tcccaccggc agcggtaaga gcaccaaggt cccggctgcg tacgcagcca    4080
agggctacaa ggtgttggtg ctcaacccct ctgttgctgc aacactgggc tttggtgctt    4140
acatgtccaa ggcccatggg gttgatccta atatcaggac cggggtgaga acaattacca    4200
ctggcagccc catcacgtac tccacctacg gcaagttcct tgccgacgcc gggtgctcag    4260
gaggtgctta tgacataata atttgtgacg agtgccactc cacggatgcc acatccatct    4320
cgggcatcgg cactgtcctt gaccaagcag agactgcggg ggcgagactg gttgtgctcg    4380
ccactgctac ccctccgggc tccgtcactg tgtcccatcc taacatcgag gaggttgctc    4440
tgtccaccac cggagagatc cccttttacg gcaaggctat cccctcgag gtgatcaagg     4500 ggggaagaca tctcatcttc tgccactcaa agaagaagtg cgacgagctc gccgcgaagc    4560
tggtcgcatt gggcatcaat gccgtggcct actaccgcgg tcttgacgtg tctgtcatcc    4620
cgaccagcgg cgatgttgtc gtcgtgtcga ccgatgctct catgactggc tttaccggcg    4680
acttcgactc tgtgatagac tgcaacacgt gtgtcactca cagtcgat tttagccttg      4740 accctacctt taccattgag acaaccacgc tccccccagga tgctgtctcc aggactcaac   4800
gccggggcag gactggcagg gggaagccag gcatctatag atttgtggca ccgggggagc    4860
gcccctccgg catgttcgac tcgtccgtcc tctgtgagtg ctatgacgcg ggctgtgctt    4920
ggtatgagct cacgcccgcc gagactacag ttaggctacg agcgtacatg aacacccgg     4980 ggcttcccgt gtgccaggac catcttggat tttgggaggg cgtctttacg ggcctcactc    5040
atatagatgc ccactttcta tcccagacaa agcagagtgg ggagaacttt ccttacctgg    5100
tagcgtacca agccaccgtg tgcgctaggg ctcaagcccc tccccatcg tgggaccaga     5160 tgcggaagtg tttgatccgc cttaaaccca ccctccatgg gccaacaccc ctgctataca    5220
gactgggcgc tgttcagaat gaagtcaccc tgacgcaccc aatcaccaaa tacatcatga    5280
catgcatgtc ggccgacctg gaggtcgtca cgagcacctg ggtgctcgtt ggcggcgtcc    5340
tggctgctct ggccgcgtat gccctgtcaa caggctgcgt ggtcatagtg ggcaggatcg    5400
tcttgtccgg gaagccggca attatacctg acagggaggt tctctaccag gagttcgatg    5460
agatggaaga gtgctctcag cacttaccgt acatcgagca agggatgatg ctcgctgagc    5520
agttcaagca gaaggccctc ggcctcctgc agaccgcgtc ccgccatgca gaggttatca    5580
cccctgctgt ccagaccaac tggcagaaac tcgaggtctt tgggcgaag cacatgtgga     5640 atttcatcag tggatacaa tacttggcgg gcctgtcaac gctgcctggt aaccccgcca     5700
ttgcttcatt gatggctttt acagctgccg tcaccagccc actaaccact ggccaaaccc    5760
tcctcttcaa catattgggg gggtgggtgg ctgcccagct cgccgccccc ggtgccgcta    5820
ccgcctttgt gggcgctggc ttagctggcg ccgcactcga cagcgttgga ctggggaagg    5880
tcctcgtgga cattcttgca ggctatgcgc gggcgtggc gggagctctt gtggcattca     5940
agatcatgag cggtgaggtc ccctccacgg aggacctggt caatctgctg cccgccatcc    6000
tctcacctgg agcccttgca gtcggtgtgg tctttgcatc aatactgcgc cggcgtgttg    6060
gcccgggcga gggggcagtg caatggatga accggctaat agccttcgcc tcccggggga    6120
accatgtttc ccccacacac tacgtgccgg agagcgatgc agccgcccgc gtcactgcca    6180
tactcagcag cctcactgta acccagctcc tgaggcgact gcatcagtgg ataagctcgg    6240
agtgtaccac tccatgctcc ggttcctggc taagggacat ctgggactgg atatgcgagg    6300
tgctgagcga ctttaagacc tggctgaaag ccaagctcat gccacaactg cctgggattc    6360
```

```
cctttgtgtc ctgccagcgc gggtataggg gggtctggcg aggagacggc attatgcaca   6420
ctcgctgcca ctgtggagct gagatcactg gacatgtcaa aaacgggacg atgaggatcg   6480
tcggtcctag gacctgcaag aacatgtgga gtgggacgtt cttcattaat gcctacacca   6540
cgggcccctg tactcccctt cctgcgccga actataagtt cgcgctgtgg agggtgtctg   6600
cagaggaata cgtggagata aggcgggtgg gggacttcca ctacgtatcg ggcatgacta   6660
ctgacaatct caaatgcccg tgccagatcc catcgcccga attttcaca  gaattggacg   6720 gggtgcgcct acataggttt gcgccccctt gcaagccctt gctgcgggag gaggtatcat   6780
tcagagtagg actccacgag tacccggtgg ggtcgcaatt accttgcgag cccgaaccgg   6840
acgtagccgt gttgacgtcc atgctcactg atccctccca tataacagca gaggcggccg   6900
ggagaaggtt ggcgagaggg tcaccccctt ctatggccag ctcctcggct agccagctgt   6960
ccgctccatc tctcaaggca acttgcaccg ccaaccatga ctcccctgac gccgagctca   7020
tagaggctaa cctcctgtgg aggcaggaga tgggcggcaa catcaccagg gttgagtcag   7080
agaacaaagt ggtgattctg gactccttcg atccgcttgt ggcagaggag gatgagcggg   7140
aggtctccgt acccgcagaa attctgcgga agtctcggag attcgcccca gccctgcccg   7200
tctgggcgcg gccggactac aaccccctgc tagtagagac gtggaaaaag cctgactacg   7260
aaccacctgt ggtccatggc tgcccgctac cacctccacg gtcccctcct gtgcctccgc   7320
ctcggaaaaa gcgtacggtg gtcctcaccg aatcaaccct acctactgcc ttggccgagc   7380
ttgccaccaa aagtttggc  agctcctcaa cttccggcat tacgggcgac aatacgacaa   7440
catcctctga gcccgcccct tctggctgcc ccccgactc  cgacgttgag tcctattctt   7500
ccatgccccc cctggagggg gagcctgggg atccggatct cagcgacggg tcatggtcga   7560
cggtcagtag tggggccgac acggaagatg tcgtgtgctg ctcaatgtct tattcctgga   7620
caggcgcact cgtcaccccg tgcgctgcgg aggaacaaaa actgcccatc aacgcactga   7680
gcaactcgtt gctacgccat cacaatctgg tgtattccac cacttcacgc agtgcttgcc   7740
aaaggaagaa gaaagtcaca tttgacagac tgcaagttct ggacagccat taccaggacg   7800
tgctcaagga ggtcaaagca gcggcgtcaa aagtgaaggc taacttgcta tccgtagagg   7860
aagcttgcag cctggcgccc ccacattcag ccaaatccaa gtttggctat ggggcaaaag   7920
acgtccgttg ccatgccaga aaggccgtag cccacatcaa ctccgtgtgg aaagaccttc   7980
tggaagacag tgtaacacca atagacacta ccatcatggc caagaacgag gttttctgcg   8040
ttcagcctga aagggggggt cgtaagccag ctcgtctcat cgtgttcccc gacctgggcg   8100
tgcgcgtgtg cgagaagatg gccctgtacg acgtggttag caagctcccc ttggccgtga   8160
tgggaagctc ctacggattc caatactcac caggacagcg ggttgaattc ctcgtgcaag   8220
cgtggaagtc caagaagacc ccgatggggc tctcgtatga tacccgctgt tttgactcca   8280
cagtcactga gagcgacatc cgtacggagg aggcaattta ccaatgttgt gacctggacc   8340
cccaagcccg cgtggccatc aagtccctca ctgagaggct ttatgttggg ggccctctta   8400
ctaattcaag gggggaaaac tgcggctacc gcaggtgccg cgcgagcaga gtactgacaa   8460
ctagctgtgg taacacactc actcgctaca tcaaggcccg gcagcctgt  cgagccgcag   8520 ggctccagga ctgcaccatg ctcgtgtgtg gcgacgactt agtcgttatc tgtgaaagtg   8580 cggggtcca  ggaggacgcg gcgagcctga gagccttcac ggaggctatg accaggtact   8640 ccgcccccc  cggggacccc ccacaaccag aatacgactt ggagcttata acatcatgct   8700
cctccaacgt gtcagtcgcc cacgacggcg ctggaaagag ggtctactac cttacccgtg   8760
```

-continued

```
accctacaac cccctcgcg agagccgcgt gggagacagc aagacacact ccagtcaatt    8820
cctggctagg caacataatc atgtttgccc ccacactgtg ggcgaggatg atactgatga    8880
cccacttctt tagcgtcctc atagccaggg atcagcttga acaggctctc aactgcgaga    8940
tctacggagc ctgctactcc atagaaccac tggatctacc tccaatcatt caaagactcc    9000
atggcctcag cgcattttca ctccacagtt actctccagg tgaaattaat agggtggccg    9060
catgcctcag aaaacttggg gtcccgccct tgcgagcttg agacaccgg gcctggagcg    9120 tccgcgctag gcttctggcc agaggaggca aggctgccat atgtggcaag tacctcttca    9180
actgggcagt aagaacaaag ctcaaactca ctccgataac ggccgctggc cggctggact    9240
tgtccggctg gttcacggct ggctacagcg ggggagacat ttatcacagc gtgtctcatg    9300
cccggccccg ctggttctgg ttttgcctac tcctgcttgc tgcaggggta ggcatctacc    9360
tcctccccaa ccgatgaaga ttgggctaac cactccaggc caataggcca ttccct        9416
```

<210> SEQ ID NO 14
<211> LENGTH: 3182
<212> TYPE: DNA
<213> ORGANISM: Artificial Sequence
<220> FEATURE:
<223> OTHER INFORMATION: Hepatitis B virus sequence

<400> SEQUENCE: 14

```
aattccacaa ccttccacca aactctgcaa gatcccagag tgagaggcct gtatttccct     60
gctggtggct ccagttcagg aacagtaaac cctgttctga ctactgcctc tcccttatcg    120
tcaatcttct cgaggattgg ggaccctgcg ctgaacatgg agaacatcac atcaggattc    180
ctaggacccc ttctcgtgtt acaggcgggg ttttcttgt tgacaagaat cctcacaata    240
ccgcagagtc tagactcgtg gtggacttct ctcaattttc taggggggaac taccgtgtgt    300 cttggccaaa attcgcagtc cccaacctcc aatcactcac caacctcttg tcctccaact    360
tgtcctggtt atcgctggat gtgtctgcgg cgttttatca tcttcctctt catcctgctg    420
ctatgcctca tcttcttgtt ggttcttctg gactatcaag gtatgttgcc cgtttgtcct    480
ctaattccag gatcctcaac aaccagcacg ggaccatgcc ggacctgcat gactactgct    540
caaggaacct ctatgtatcc ctcctgttgc tgtaccaaac cttcggacgg aaattgcacc    600
tgtattccca tcccatcatc ctgggctttc ggaaaattcc tatgggagtg ggcctcagcc    660
cgtttctcct ggctcagttt actagtgcca tttgttcagt ggttcgtagg ctttccccc    720 actgtttggc tttcagttat atggatgatg tggtattggg ggccaagtct gtacagcatc    780
ttgagtccct ttttaccgct gttaccaatt ttcttttgtc tttgggtata catttaaacc    840
ctaacaaaac aaagagatgg ggttactctc taaattttat gggttatgtc attggatgtt    900
atgggtcctt gccacaagaa cacatcatac aaaaaatcaa agaatgtttt agaaaacttc    960
ctattaacag gcctattgat tggaaagtat gtcaacgaat tgtgggtctt ttgggttttg   1020 ctgcccctt tacacaatgt ggttatcctg cgttgatgcc tttgtatgca tgtattcaat   1080
ctaagcaggc tttcactttc tcgccaactt acaaggcctt tctgtgtaaa caatacctga   1140
acctttaccc cgttgcccgg caacggccag gtctgtgcca agtgtttgct gacgcaaccc   1200
ccactggctg gggcttggtc atgggccatc agcgcatgcg tggaaccttt tcggctcctc   1260
tgccgatcca tactgcggaa ctcctagccg cttgttttgc tcgcagcagg tctggagcaa   1320
acattatcgg gactgataac tctgttgtcc tatcccgcaa atatacatcg tttccatggc   1380
```

```
tgctaggctg tgctgccaac tggatcctgc gcgggacgtc ctttgtttac gtcccgtcgg    1440
cgctgaatcc tgcggacgac ccttctcggg gtcgcttggg actctctcgt ccccttctcc    1500
gtctgccgtt ccgaccgacc acggggcgca cctctcttta cgcggactcc ccgtctgtgc    1560
cttctcatct gccggaccgt gtgcacttcg cttcacctct gcacgtcgca tggagaccac    1620
cgtgaacgcc caccaaatat tgcccaaggt cttacataag aggactcttg gactctcagc    1680
aatgtcaacg accgaccttg aggcatactt caaagactgt ttgtttaaag actgggagga    1740
gttgggggag gagattaggt taaaggtctt tgtactagga ggctgtaggc ataaattggt    1800
ctgcgcacca gcaccatgca actttttcac ctctgcctaa tcatctcttg ttcatgtcct    1860
actgttcaag cctccaagct gtgccttggg tggctttggg gcatggacat cgacccttat    1920
aaagaatttg gagctactgt ggagttactc tcgtttttgc cttctgactt ctttccttca    1980
gtacgagatc ttctagatac cgcctcagct ctgtatcggg aagccttaga gtctcctgag    2040
cattgttcac ctcaccatac tgcactcagg caagcaattc tttgctgggg ggaactaatg    2100
actctagcta cctgggtggg tgttaatttg gaagatccag cgtctagaga cctagtagtc    2160
agttatgtca acactaatat gggcctaaag ttcaggcaac tcttgtggtt tcacatttct    2220
tgtctcactt ttggaagaga aacagttata gagtatttgg tgtctttcgg agtgtggatt    2280
cgcactcctc cagcttatag accaccaaat gcccctatcc tatcaacact tccggagact    2340
actgttgtta gacgacgagg caggtcccct agaagaagaa ctccctcgcc tcgcagacga    2400
aggtctcaat cgccgcgtcg cagaagatct caatctcggg aatctcaatg ttagtattcc    2460
ttggactcat aaggtgggga actttactgg gctttattct tctactgtac ctgtctttaa    2520
tcctcattgg aaaacaccat cttttcctaa tatacattta caccaagaca ttatcaaaaa    2580
atgtgaacag tttgtaggcc cactcacagt taatgagaaa agaagattgc aattgattat    2640
gcctgccagg ttttatccaa aggttaccaa atatttacca ttggataagg gtattaaacc    2700
ttattatcca gaacatctag ttaatcatta cttccaaact agacactatt tacacactct    2760
atggaaggcg ggtatattat ataagagaga acaacacat agcgcctcat tttgtgggtc    2820
accatattct tgggaacaag atctacagca tggggcagaa tctttccacc agcaatcctc    2880
tgggattctt tcccgaccac cagttggatc cagccttcag agcaaacacc gcaaatccag    2940
attgggactt caatcccaac aaggacacct ggccagacgc caacaaggta ggagctggag    3000
cattcgggct gggtttcacc ccaccgcacg gaggcctttt ggggtggagc cctcaggctc    3060
agggcatact acaaactttg ccagcaaatc cgcctcctgc ctccaccaat cgccagtcag    3120
gaaggcagcc taccccgctg tctccacctt tgagaaacac tcatcctcag gccatgcagt    3180
gg                                                                    3182
```

<210> SEQ ID NO 15
<211> LENGTH: 7478
<212> TYPE: DNA
<213> ORGANISM: Artificial Sequence
<220> FEATURE:
<223> OTHER INFORMATION: Hepatitis A virus sequence

<400> SEQUENCE: 15

```
ttcaagaggg gtctccggag gtttccggag cccctcttgg aagtccatgg tgaggggact      60
tgatacctca ccgccgtttg cctaggctat aggctaaatt tccctttccc tgtccctccc     120
ttatttccct tgttttgct tgtaaatatt aattcctgca ggttcaggt tctttaatct      180 gtttctctat aagaacactc aattttcacg ctttctgtct tctttcttcc agggctctcc    240
```

```
ccttgccctaggctctggccgttgcgcccggcggggtcaactccatgattagcatggagc      300
tgtaggagtctaaattggggacgcagatgtttgggacgtcaccttgcagtgttaacttgg      360
ctctcatgaacctctttgatcttccacaaggggtaggctacgggtgaaacctcttaggct      420
aatacttctatgaagagatgctttggatagggtaacagcggcggatattggtgagttgtt      480
aagacaaaaaccattcaacgccggaggactggctctcatccagtggatgcattgagtgga      540
ttgattgtcagggctgtctctaggtttaatctcagacctctctgtgcttagggcaaacac      600
catttggcctaaaatgggatcctgtgagaggggtccctccattgacagctggactgttc      660
tttgggcctatgtggtgtttgcctctgaggtactcagggcatttaggttttcctca        720
ttcttaaacaataatgaatatgtccaaacaaggaattttcagactgttgggagtggcct      780
tgaccacatcctgtctttggcagatattgaggaagagcaaatgattcagtccgttgatag      840
gactgcagtgactggagcttcttacttcacttctgtggaccaatcttcagttcatactgc      900
tgaggttggctcacatcaaattgaacctttgaaaacctctgttgataaactggttctaa      960
gaaaactcaggggaaaagtttttcctgatcattctgctgattggctcactacacatgc     1020
tctctttcatgaagttgcaaaattggatgtggtgaaactactgtataatgagcagtttgc     1080
cgtccaaggtttgttgagataccatacatatgcaagatttggcattgagattcaagttca     1140
gataaatcccacacccttcagcaaggaggactaatttgtgccatggttcctggtgacca     1200
aagttatggttcaatagcatccttgactgtttatcctcatggtctgttaaattgcaatat     1260
caacaatgtagttagaataaaggttccatttatttatactagaggtgcttatcattttaa     1320
agatccacagtacccagttggggaattgacaatcagagttggtcagagttgaatattgg     1380
aacaggaactttcagcttacacttcactcaatgttttagctaggtttacagatttggagtt     1440
gcatggattaactcctctttctacacagatgatgagaaatgaatttagggtcagtactac     1500
tgaaaatgttgtaaatttgtcaaattatgaagatgcaaggcaaaaatgtcttttgctttt     1560
ggatcaggaagattggaagtctgatccttcccaaggtggtggaattaaaattactcattt     1620
tactacctggacatccattcaaccttagctgctcagtttccatttaatgcttcagattc     1680
agttggacaacaaattaaagttattccagtggacccatacttttttccaaatgacaaacac     1740
taatcctgatcaaaaatgtaaactgccttggcctctattgtcagatgttctgcttttg      1800
gaggggagatcttgttttttgattttcaggtttttccaaccaaatatcattcaggtagact     1860
gttgttttgttttgttcctgggaatgagttaatagatgttactggaattacattaaaaca     1920
ggcaactactgctccttgtgcagtgatggacattacaggagtgcagtcaaccttgagatt     1980
tcgtgttcctggattctgatacaccttatcgagtgaataggtacacgaagtcagcaca      2040
tcaaaaggtgagtacactgccattgggaagcttattgtgtattgttatacagactgac     2100
ttctccttctaatgttgcctctcatgttagagttaatgtttatctttcagcaattaatttt     2160
ggaatgttttgctcctcttttaccatgctatggatgttactacacaggttgagatgattc     2220
aggaggtttctcaacaacagtttctacagagcagaatgttcctgatccccaagttgggat     2280
aacaaccatgagggatttaaaaggaaaagccaataggggaaagatggatgtttcaggagt     2340
gcaagcacctcgtgggagctatcagcaacaattgaacgatccagttttagcaaagaaagt     2400
acctgagacatttcctgaattgaagcctggagagtccagacatacatcagatcacatgtc     2460
tatttataaattcatgggaaggtctcattttttgtgcactttactttcaattcaaataa     2520
taaagagtacacatttccaataaccctgtcttcgacttctaatcctcctcatggtttacc     2580
```

```
atcaacatta aggtggttct tcaatttgtt tcagttgtat agaggaccat tggatttaac    2640
aattataatc acaggagcca ctgatgtgga tggtatggcc tggtttactc cagtgggcct    2700
tgctgtcgac ccttgggtgg aaaaggagtc agctttgtct attgattata aaactgccct    2760
tggagctgtt agatttaata caagaagaac aggaaacatt caaattagat tgccgtggta    2820
ttcttatttg tatgccgtgt ctggagcact ggatggcttg gggataagaa cagattctac    2880
atttggattg tttctattcg agattgcaaa ttacaatcat tctgatgaat atttgtcctt    2940
cagttgttat ttgtctgtca cagagcaatc agagttctat tttcctagag ctccattaaa    3000
ttcaaatgct atgttgtcca ctgaatccat gatgagtaga attgcagctg gagacttgga    3060
gtcatcagtg gatgatccca gatcagagga ggatagaaga tttgagagtc atatagaatg    3120
taggaaacca tacaaagaat tgagactgga ggttgggaaa caaagactca aatatgctca    3180
ggaagagtta tcaaatgaag tgcttccacc tcctaggaaa atgaaggggt tattttcaca    3240
agctaaaatt tctctttttt atactgagga gcatgaaata atgaagtttt cttggagagg    3300
agtgactgct gatactaggg ctttgagaag atttggattc tctctggctg ctggtagaag    3360
tgtgtggact cttgaaatgg atgctggagt tcttactgga agattgatca gattgaatga    3420
tgagaaatgg acagaaatga aggatgataa gattgtttca ttaattgaaa agttcacaag    3480
caataaatat tggtctaaag tgaattttcc acatggaatg ttggatcttg aagaaattgc    3540
tgccaattct aaggattttc caaatatgtc tgagacagat ttgtgtttcc tgttacattg    3600
gctaaatcca agaaaatca atttagcaga tagaatgctt ggattgtctg gagtgcagga    3660
aattaaggaa cagggtgttg gactgatagc agagtgtaga actttcttgg attctattgc    3720
tgggactttg aaatctatga tgtttgggtt tcatcattct gtgactgttg aaattataaa    3780
tactgtgctt tgttttgtta agagtggaat cctgctttat gtcatacaac aattgaacca    3840
agatgaacac tctcacataa ttggtttgtt gagagttatg aattatgcag atattggctg    3900
ttcagttatt tcatgtggta agtttttttc caaaatgtta gaaacagttt ttaattggca    3960
aatggattct agaatgatgg agctgaggac tcagagcttc tctaattggt taagagatat    4020
ttgttcagga attactattt ttaaaagttt taaggatgcc atatattggt tatatacaaa    4080
attgaaggat ttttatgaag taaattatgg caagaaaaag gatattctta atattctcaa    4140
agataatcag caaaaaatag aaaaagccat tgaagaagca gacaattttt gcattttgca    4200
aattcaagat gtagagaaat ttgatcagta tcagaaaggg gttgatttaa tacaaaagct    4260
gagaactgtc cattcaatgg cgcaagttga ccccaatttg ggggttcatt tgtcacctct    4320
cagagattgc atagcaagag tccaccaaaa gctcaagaat cttggatcta taaatcaggc    4380
catggtaaca agatgtgagc cagttgtttg ctatttgtat ggcaaaagag ggggagggaa    4440
aagcttgact tcaattgcat tgcaaccaaa atttgtaaa cactatggtg ttgaacctga    4500
gaaaatatt tacaccaaac ctgtggcctc agattattgg gatggatata gtggacaatt    4560
agtttgcatt attgatgata ttggccaaaa cacaacagat gaagattggt cagatttttg    4620
tcaattagtg tcaggatgcc caatgagatt gaatatggct tctctagagg agaagggcag    4680
acattttcc tctccttta taatagcaac ttcaaattgg tcaaatccaa gtccaaaaac    4740
agttatgtt aaggaagcaa ttgatcgtag gcttcatttt aaggttgaag ttaaacctgc    4800
ttcattttt aaaatcctc acaatgatat gttgaatgtt aatttggcca aaacaaatga    4860
tgcaattaag gacatgtctt gtgttgattt aataatggat ggacacaata tttcattgat    4920
ggatttactt agttccttag tgatgacagt tgaaattagg aaacagaata tgagtgaatt    4980
```

-continued

```
catggagttg tggtctcagg gaatttcaga tgatgacaat gatagtgcag tggctgagtt      5040
tttccagtct tttccatctg gtgaaccatc aaattggaag ttatctagtt ttttccaatc      5100
tgtcactaat cacaagtggg ttgctgtggg agctgcagtt ggcattcttg gagtgcttgt      5160
gggaggatgg tttgtgtata agcatttttc ccgcaaagag gaagaaccaa ttccagctga      5220
aggggtttat catggcgtga ctaagcccaa acaagtgatt aaattggatg cagatccagt      5280
agagtcccag tcaactctag aaatagcagg attagttagg aaaaatctgg ttcagtttgg      5340
agttggtgag aaaaatggat gtgtgagatg ggtcatgaat gccttaggag tgaaggatga      5400
ttggttgtta gtaccttctc atgcttataa atttgaaaag gattatgaaa tgatggagtt      5460
ttacttcaat agaggtggaa cttactattc aatttcagct ggtaatgttg ttattcaatc      5520
tttagatgtg ggatttcaag atgttgtttt aatgaaggtt cctacaattc ccaagtttag      5580
agatattact caacacttta ttaagaaagg agatgtgcct agagccttaa atcgcttggc      5640
aacattagtg acaaccgtta atggaactcc tatgttaatt tctgagggac cattaaagat      5700
ggaagaaaaa gccacttatg ttcataagaa gaatgatggt actacagttg atttgactgt      5760
agatcaggca tggagaggaa aaggtgaagg tcttcctgga atgtgtggtg gggccctagt      5820
gtcatcaaat cagtccatac agaatgcaat tttgggtatt catgttgctg gaggaaattc      5880
aattcttgtg gcaaagctgg ttactcaaga aatgtttcaa acattgata agaaaattga      5940 aagtcagaga ataatgaaag tggaatttac tcaatgttca atgaatgtag tctccaaaac      6000 gcttttaga aagagtccca ttcatcacca cattgataaa accatgatta attttcctgc      6060
agctatgcct ttctctaaag ctgaaattga tccaatggct atgatgttgt ccaaatattc      6120
attacctatt gtggaggaac cagaggatta caaggaagct tcagtttttt atcaaaacaa      6180
aatagtaggc aagactcagc tagttgatga ctttttagat cttgatatgg ctattacagg      6240
ggctccaggc attgatgcta tcaatatgga ttcatctcct gggtttcctt atgttcaaga      6300
aaaattgacc aaaagagatt aatttggtt ggatgaaaat ggtttgctgt taggagttca      6360
cccaagattg gcccagagaa tttttattaa tactgtcatg atggaaaatt gttctgactt      6420
agatgttgtt tttacaactt gtccaaaaga tgaattgaga ccattagaga agttttggga      6480
atcaaaaaca agagccattg atgcttgtcc tttggattat acaattctat gtcgaatgta      6540
ttggggtcca gctatcagtt atttccattt gaatccaggg tttcacacag gtgttgctat      6600
tggcatagat cctgatagac agtgggatga attatttaaa acaatgataa gatttggaga      6660
tgttggtctt gatttagatt tctctgcttt tgatgccagt cttagtccat ttatgattag      6720
ggaagcaggg agaatcatga gtgaattatc tggaacacca tctcattttg gaacagctct      6780
tatcaatact atcattatt ctaaacatct gctgtacaac tgttgttatc atgtttgtgg      6840
ttcaatgcct tctgggtctc cttgcacagc tttgttgaat tcaattatta ataatattaa      6900
tctgtattat gtgttttcta aaatatttgg aaagtctcca gttttctttt gtcaagcttt      6960
gaggatcctt tgttacggag atgatgtttt gatagttttt tccagagatg ttcaaattga      7020
caatcttgac ttgattggac agaaaattgt agatgagttc aaaaaacttg gcatgacagc      7080
cacctcagct gataaaaatg tgcctcaact gaagccagtt tcagaattga cttttctcaa      7140
aagatctttc aatttggtgg aggatagaat tagacctgca atttcagaaa agacaatttg      7200
gtctttgatg gcttggcaga gaagtaacgc tgagtttgag cagaatttag aaaatgctca      7260
gtggtttgct tttatgcatg gctatgagtt ctatcagaaa ttttattatt ttgttcagtc      7320
```

-continued

```
ctgtttggag aaagagatga tagaatatag acttaaatct tatgattggt ggagaatgag      7380
attttatgac cagtgtttca tttgtgacct ttcatgattt gtttaaacaa attttcttac      7440
tctttctgag gtttgtttat ttcttttgtc cgctaact                               7478
```